(12) United States Patent
Guillemont et al.

US008318736B2

(10) Patent No.: US 8,318,736 B2
(45) Date of Patent: Nov. 27, 2012

(54) HIV INHIBITING 5,6-SUBSTITUTED PYRIMIDINES

(75) Inventors: Jerôme Emile Georges Guillemont, Andé (FR); Céline Isabelle Mordant, Toulouse (FR); Benoit Antoine Schmitt, Mechelen (BE)

(73) Assignee: Janssen R&D Ireland (IE)

( * ) Notice: Subject to any disclaimer, the term of this patent is extended or adjusted under 35 U.S.C. 154(b) by 378 days.

(21) Appl. No.: 12/521,379

(22) PCT Filed: Dec. 28, 2007

(86) PCT No.: PCT/EP2007/064606
§ 371 (c)(1),
(2), (4) Date: Jun. 26, 2009

(87) PCT Pub. No.: WO2008/080965
PCT Pub. Date: Jul. 10, 2008

(65) Prior Publication Data
US 2010/0261722 A1 Oct. 14, 2010

(30) Foreign Application Priority Data
Dec. 29, 2006 (EP) .................................... 06127328

(51) Int. Cl.
A61K 31/535 (2006.01)
A61K 31/497 (2006.01)
A61K 31/505 (2006.01)
C07D 239/02 (2006.01)
C07D 401/08 (2006.01)
C07D 413/08 (2006.01)

(52) U.S. Cl. ................ 514/235.8; 514/252.14; 514/275; 544/122; 544/323; 544/324

(58) Field of Classification Search ............... 514/235.8, 514/275, 252.14; 544/324, 122, 323
See application file for complete search history.

(56) References Cited

U.S. PATENT DOCUMENTS

| 3,459,731 | A | 8/1969 | Gramera et al. | |
|---|---|---|---|---|
| 6,593,326 | B1 | 7/2003 | Bradbury et al. | |
| 7,504,396 | B2 | 3/2009 | Nunes et al. | |
| 7,531,548 | B2 * | 5/2009 | Guillemont et al. | 514/272 |
| 2003/0036543 | A1 | 2/2003 | Bebbington | |
| 2005/0209221 | A1 | 9/2005 | Nunes et al. | |
| 2008/0262007 | A1 | 10/2008 | Guillemont et al. | |
| 2009/0181993 | A1 | 7/2009 | Guillemont et al. | |
| 2010/0016317 | A1 | 1/2010 | Guillemont et al. | |
| 2010/0168104 | A1 | 7/2010 | Guillemont et al. | |

FOREIGN PATENT DOCUMENTS

| EP | 0834507 B2 | 4/1998 |
|---|---|---|
| WO | WO-97/018839 A1 | 5/1997 |
| WO | WO-99/50250 A1 | 10/1999 |
| WO | WO-99/050256 A1 | 10/1999 |
| WO | WO-00/27825 A1 | 5/2000 |
| WO | WO-00/039101 A1 | 7/2000 |
| WO | WO 01/85700 | 11/2001 |
| WO | WO-03/016306 A1 | 2/2003 |
| WO | WO-03/063794 A2 | 8/2003 |
| WO | WO-2004/046143 A1 | 6/2004 |
| WO | WO-2005/009443 A1 | 2/2005 |
| WO | WO-2006/035067 A1 | 4/2006 |
| WO | WO-2006/035067 A2 | 4/2006 |
| WO | WO-2006/035069 A1 | 4/2006 |
| WO | WO-2007/113254 A1 | 10/2007 |
| WO | WO-2008/080964 A1 | 7/2008 |

OTHER PUBLICATIONS

ScienceDirect; Advanced Drug Delivery Reviews; vol. 48, issue 1; May 16, 2001.*
In the United States Patent and Trademark Office, Final-Office Action in re: U.S. Appl. No. 11/575,818, dated Feb. 2, 2011. 6 pages.
In the United States Patent and Trademark Office, Final-Office Action in re: U.S. Appl. No. 11/576,315, dated Feb. 2, 2011, 6 pages.
In the United States Patent and Trademark Office, Final-Office Action in re: U.S. Appl. No. 12/294,692, dated May 13, 2011, 10 pages.
In the United States Patent and Trademark Office, Final-Office Action in re: U.S. Appl. No. 12/521,189, dated Apr. 10, 2012, 11 pages.
In the United States Patent and Trademark Office, Final-Office Action in re: U.S. Appl. No. 11/575,818, dated Aug. 2, 2010, 7 pages.
In the United States Patent and Trademark Office, Final-Office Action in re: U.S. Appl. No. 11/576,315, dated Aug. 5, 2010, 7 pages.
In the United States Patent and Trademark Office, Final-Office Action in re: U.S. Appl. No. 12/294,692, dated Nov. 26, 2010, 8 pages.
In the United States Patent and Trademark Office, Final-Office Action in re: U.S. Appl. No. 12/521,189, dated Sep. 23, 2011, 15 pages.

(Continued)

*Primary Examiner* — James O Wilson
*Assistant Examiner* — Ebenezer O Sackey
(74) *Attorney, Agent, or Firm* — Toni-Junell Herbert

(57) ABSTRACT

HIV replication inhibitors of formula

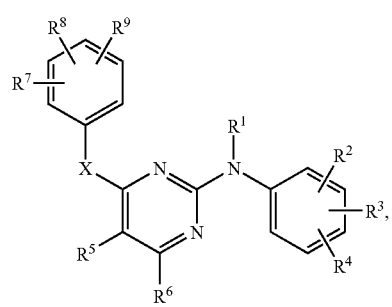

(I)

wherein R1, R2, R3, R4, R5, R6, R7, R8, R9 and X have specific definitions, and pharmaceutical compositions containing these compounds as active ingredient and processes for preparing said compounds and compositions.

12 Claims, No Drawings

OTHER PUBLICATIONS

International Search Report from PCT/EP2005/054932, dated Sep. 12, 2005.
International Search Report from PCT/EP2005/054930, dated Jun. 20, 2006.
International Search Report from PCT/EP2007/053111, dated Aug. 14, 2007.
International Search Report from PCT/EP2007/064605, dated May 6, 2008.
International Search Report from PCT/EP2007/064606, dated Jul. 14, 2008.
Ludovici, D. et al., "Evolution of Anti-HIV Drug Candidates. Part 3: Diarylpyrimidine (DAPY) Analogues"; *Bioorganic & Medicinal Chemistry Letters*, 2001; 11:2235-2239.
Nogradi, N, "Dimethyl-p-Cyclodextrin," *Drugs of the Future*, 9(8):577-578, 1984.

* cited by examiner

HIV INHIBITING 5,6-SUBSTITUTED PYRIMIDINES

CROSS-REFERENCE TO RELATED APPLICATIONS

This application is a U.S. National Phase Application of International Application No. PCT/EP2007/064606, filed Dec. 28, 2007, which claims priority from European Patent Application No. 06127328.0 filed Dec. 29, 2006, the disclosure of which is hereby incorporated by reference in its entirety.

This invention concerns 5,6-substituted pyrimidine derivatives having HIV (Human Immunodeficiency Virus) replication inhibiting properties, the preparation thereof and pharmaceutical compositions comprising these compounds.

Initially, treatment of HIV infection consisted of monotherapy with nucleoside derivatives and although successful in suppressing viral replication, these drugs quickly lost their effectiveness due to the emergence of drug-resistant strains. It became clear that a high mutation rate combined with rapid replication made HIV a particularly challenging target for antiviral therapy. The introduction of combination therapy of two or more anti-HIV agents improved therapeutic outcome. Significant progress was made by the introduction of HAART (Highly Active Anti-Retroviral Therapy) that resulted in a powerful and sustained virus suppression. HAART typically involves combinations of nucleoside or nucleotide reverse transcriptase inhibitors (NRTIs or NtRTIs respectively) with a non-nucleoside reverse transcriptase inhibitor (NNRTI) or a protease inhibitor (PI). Current guidelines for antiretroviral therapy recommend such triple combination therapy regimen even for initial treatment. These multidrug therapies however do not completely eliminate HIV and long-term treatment usually results in multidrug resistance. It also has been shown that resistant virus is carried over to newly infected individuals, resulting in severely limited therapy options for these drug-naive patients.

Therefore there is a continued need for new combinations of agents that are effective against HIV. New types of anti-HIV effective active ingredients, differing in chemical structure and activity profile may find use in new types of combination therapy Finding such active ingredients therefore is a highly desirable goal to achieve.

The present invention is aimed at providing particular novel series of pyrimidine derivatives having HIV replication inhibiting properties. WO 99/50250, WO 00/27825, WO 01/85700, and WO 06/035067 disclose certain classes of substituted aminopyrimidines having HIV replication inhibiting properties.

The compounds of the invention differ from prior art compounds in structure, pharmacological activity and/or pharmacological potency. It has been found that the introduction of certain substituents in the 5-position and 6-position of specifically substituted pyrimidines results in compounds not only acting favorably by their capability to inhibit the replication of Human Immunodeficiency Virus (HIV), but also by their improved ability to inhibit the replication of mutant strains, in particular of strains that have become resistant to one or more known NNRTI drugs, which strains are referred to as drug- or multidrug-resistant HIV strains.

Thus, in one aspect, the present invention concerns compounds of formula

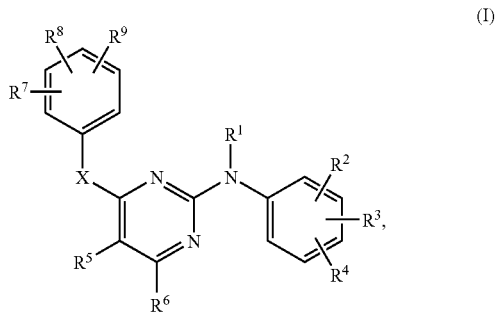

(I)

the pharmaceutically acceptable addition salts, the pharmaceutically acceptable solvates, and stereochemically isomeric forms thereof, wherein:

each $R^1$ independently is hydrogen; aryl; formyl; $C_{1-6}$alkylcarbonyl; $C_{1-6}$alkyl; $C_{1-6}$alkyloxycarbonyl;

$R^2$, $R^3$, $R^7$ and $R^8$ independently are hydrogen; hydroxy; halo; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^{10}$; $C_{1-6}$alkyl optionally substituted with halo, cyano or —C(=O)$R^{10}$; $C_{2-6}$alkenyl optionally substituted with halo, cyano or —C(=O)$R^{10}$; $C_{2-6}$alkynyl optionally substituted with halo, cyano or —C(=O)$R^{10}$;

$R^4$ and $R^9$ independently are hydroxy; halo; $C_{3-7}$cycloalkyl; $C_{1-6}$alkyloxy; carboxyl; $C_{1-6}$alkyloxycarbonyl; formyl; cyano; nitro; amino; mono- or di($C_{1-6}$alkyl)amino; polyhalo$C_{1-6}$alkyl; polyhalo$C_{1-6}$alkyloxy; —C(=O)$R^{10}$; cyano; —S(=O)$_t$$R^{10}$; —NH—S(=O)$_2$$R^{10}$; —NHC(=O)H; —C(=O)NHNH$_2$; —NHC(=0)$R^{10}$; Het; $C_{1-6}$alkyl optionally substituted with halo, cyano, amino, mono- or di($C_{1-6}$alkyl)amino, —C(=O)-12$^{10}$, Het or with $C_{1-6}$alkyloxy; $C_{2-6}$alkenyl optionally substituted with halo, cyano, amino, mono- or di($C_{1-6}$alkyl)amino, —C(=0)—$R^{10}$, Het or with $C_{1-6}$alkyloxy; $C_{2-6}$alkynyl optionally substituted with halo, cyano, amino, mono- or di($C_{1-6}$alkyl)amino, —C(=0)—$R^{10}$, Het or with $C_{1-6}$alkyloxy;

$R^5$ is $C_{2-6}$alkenyl or $C_{2-6}$alkynyl both substituted with cyano, aminocarbonyl, mono- or di($C_{1-6}$alkyl)aminocarbonyl, aryl, pyridyl, thienyl, furanyl, or with one or two $C_{1-6}$alkyloxy groups; or $R^5$ is Het; —C(=0)NR$^{5a}$R$^{5b}$; or —CH(OR$^{5c}$)R$^{5d}$; wherein $R^{5a}$ is $C_{1-6}$alkyloxy; $C_{2-6}$alkenyl; $C_{3-7}$cycloalkyl; or $C_{1-6}$alkyl substituted with hydroxy, amino, mono- or di($C_{1-6}$alkyl)amino, $C_{1-6}$alkylcarbonylamino, halo, cyano, aryl, pyridyl, thienyl, furanyl, tetrahydrofuranyl, pyrrolidinyl, piperidinyl, morpholinyl, piperazinyl, piperazinyl optionally substituted with $C_{1-6}$alkyl, $C_{1-6}$alkylcarbonyl, or with hydroxy$C_{1-6}$alkyl; or $R^{5a}$ is $C_{1-6}$alkyl substituted with one or two $C_{1-6}$alkyloxy;

$R^{5b}$ is hydrogen or $C_{1-6}$alkyl; or $R^{5a}$ and $R^{5b}$ taken together with the nitrogen atom to which they are substituted form pyrrolidinyl; piperidinyl optionally substituted with aminocarbonyl, hydroxy, or with $C_{1-6}$alkyloxy; morpholinyl; piperazinyl; piperazinyl optionally substituted with $C_{1-6}$alkyl, $C_{1-6}$alkylcarbonyl, or with hydroxy$C_{1-6}$alkyl;

R5c is hydrogen, $C_{1-6}$alkyl, Het;
$R^{5d}$ is $C_{1-6}$alkyl, $C_{2-6}$alkenyl, $C_{2-6}$alkynyl, aryl, or Het;
$R^6$ is $C_{1-6}$alkoxy$C_{1-6}$alkyl;
each $R^{10}$ independently is $C_{1-6}$alkyl, amino, mono- or di($C_{1-6}$alkyl)amino or polyhalo$C_{1-6}$alkyl;
X is —$NR^1$—, —O—, —$CH_2$—, or —S—;
each r independently is 1 or 2;
each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from $C_{1-6}$alkyl, halo, hydroxy, cyano, $C_{1-6}$alkyloxy, and $C_{2-6}$alkenyl substituted with halo, hydroxy or with cyano;
each aryl independently is phenyl or phenyl substituted with one, two, three, four or five substituents each independently selected from halo, hydroxy, mercapto, C1-6alkyl, C2-6alkenyl, C2-6alkynyl, hydroxyC1-6alkyl, aminoC1-6alkyl, mono or di(C1-6alkyl)carbonyl, C1-6alkylcarbonyl, C3-7cycloalkyl, C1-6alkyloxy, phenylC1-6alkyloxy, C1-6alkyloxycarbonyl, aminosulfonyl, C1-6alkylthio, C1-6alkylsulfonyl, cyano, nitro, polyhaloC1-6alkyl, polyhaloC1-6alkyloxy, aminocarbonyl, phenyl, or Het.

As used hereinbefore or hereinafter $C_{1-4}$alkyl as a group or part of a group defines straight or branched chain saturated hydrocarbon radicals having from 1 to 4 carbon atoms such as methyl, ethyl, 1-propyl, 2-propyl, 1-butyl, 2-butyl, 2-methylpropyl, t.butyl; $C_{1-6}$alkyl as a group or part of a group defines straight or branched chain saturated hydrocarbon radicals having from 1 to 6 carbon atoms such as the group defined for $C_{1-4}$alkyl and 1-pentyl, 2-pentyl, 1-hexyl, 2-hexyl, 3-hexyl, 2-methylbutyl, 3-methylpentyl, and the like; $C_{1-2}$alkyl defines methyl or ethyl; $C_{3-7}$cycloalkyl is generic to cyclopropyl, cyclobutyl, cyclopentyl, cyclohexyl and cycloheptyl. Preferred amongst $C_{1-6}$alkyl are $C_{1-4}$alkyl or $C_{1-2}$alkyl. Preferred amongst $C_{3-7}$cycloalkyl are cyclopentyl or cyclohexyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 1-pentenyl, 2-pentenyl, 3-pentenyl, 2-methyl-1-butenyl, 1-hexenyl, 2-hexenyl, 3-hexenyl, 4-hexenyl, 2-methyl-2-pentenyl, 1,2-dimethyl-1-butenyl and the like. Preferred are $C_{2-6}$alkenyls having one double bond. Of interest amongst $C_{2-6}$alkenyl radicals are the $C_{2-4}$alkenyl radicals. The term "$C_{3-6}$alkenyl" is as $C_{2-6}$alkenyl but is limited to unsaturated hydrocarbon radicals having from 3 to 6 carbon atoms. In the instances where a $C_{3-6}$alkenyl is linked to a heteroatom, the carbon atom linked to the heteroatom by preference is saturated. This e.g. is the case for $C_{3-6}$alkenyl substituted with hydroxy where the hydroxy preferably is not on a double bonded carbon atom.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-methyl-2-propynyl, 2-pentynyl, 3-pentynyl, 2-hexynyl, 3-hexynyl, 4-hexynyl, 2-methyl-2-butynyl, 2-methyl-2-pentynyl and the like. Preferred are $C_{2-6}$alkynyls having one triple bond. Of interest amongst $C_{2-6}$alkynyl radicals are the $C_{2-4}$alkynyl radicals. The term "$C_{3-6}$alkynyl" is as $C_{2-6}$alkynyl but is limited to unsaturated hydrocarbon radicals with at least one triple bond having from 3 to 6 carbon atoms. In the instances where a $C_{3-6}$alkynyl is linked to a heteroatom, the carbon atom linked to the heteroatom by preference is saturated. This e.g. is the case for $C_{3-6}$alkynyl substituted with hydroxy where the hydroxy preferably is not on a triple bonded carbon atom.

As used herein before, the term (=O) refers to a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term "halo" is generic to fluoro, chloro, bromo or iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoro$C_{1-6}$ alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

Any of the heterocycles mentioned in the definitions of Het is meant to comprise any isomer such as for example oxadiazole may be 1,2,4-oxadiazole, 1,3,4-oxadiazole, or 1,2,3-oxadiazole; likewise for thiadiazole, which may be 1,2,4-thiadiazole, 1,3,4-thiadiazole, or 1,2,3-thiadiazole; similarly, pyrrole may be 1H-pyrrole, or 2H-pyrrole. The group Het can be oxazolyl or thiazoyl, which preferably are 1,3-oxazolyl or 1,3-thiazolyl, respectively.

Any pyrrolidinyl, piperidinyl, morpholinyl, piperazinyl, piperazinyl in particular is substituted to the remainder of the molecule via its nitrogen atom. Any piperazinyl being substituted such as with $C_{1-6}$alkyl, $C_{1-6}$alkylcarbonyl, or with hydroxy$C_{1-6}$alkyl, is preferably substituted at the nitrogen through which the piperazine is not connected to the remainder of the molecule (in many instances the 4-nitrogen).

In one embodiment each Het independently is pyridyl, thienyl, furanyl, oxazolyl, or thiazolyl.

Whenever a radical occurs in the definition of the compounds of formula (I) or in any of the subgroups specified herein, said radical independently is as specified above in the definition of the compounds of formulas (I) or in the more restricted definitions as specified hereinafter.

It should also be noted that the radical positions on any molecular moiety used in the definitions may be anywhere on such moiety as long as it is chemically stable. For instance pyridine includes 2-pyridine, 3-pyridine and 4-pyridine; pentyl includes 1-pentyl, 2-pentyl and 3-pentyl.

When any variable (e.g. halogen, $C_{1-6}$alkyl, aryl, Het, etc.) occurs more than one time in any moiety, each definition is independent. Any limited definitions of the radicals specified herein are meant to be applicable to the group of compounds of formula (I) as well as to any subgroup defined or mentioned herein. Lines drawn from substituents into ring systems indicate that the bond may be attached to any of the suitable ring atoms.

The pharmaceutically acceptable addition salt forms, which the compounds of the present invention are able to form, can conveniently be prepared using the appropriate acids, such as, for example, inorganic acids such as hydrohalic acids, e.g. hydrochloric or hydrobromic acid, sulfuric, hemisulphuric, nitric, phosphoric, and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzene-sulfonic, p-toluenesulfonic, cyclamic, salicylic, p-amino-salicylic, pamoic, and the like acids. Conversely said acid addition salt forms can be converted into the free base form by treatment with an appropriate base.

The compounds of formula (I) containing acidic protons may be converted into their pharmaceutically acceptable metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary, and tertiary aliphatic and aromatic amines such as methylamine, ethylamine, propylamine, isopropylamine, the four butylamine isomers, dimethyl-amine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term "pharmaceutically acceptable solvate" is meant to comprise hydrates and solvent addition forms that the compounds of formula (I), including stereoisomeric forms thereof, can form. Examples of such solvates are e.g. hydrates, alcoholates, such as methanolates, ethanolates, i.propanolates, n.propanolates, and the like.

The compounds of formula (I) thereof may contain one or more centers of chirality and may exist as stereochemically isomeric forms. Of special interest are those compounds of formula (I) that are stereochemically pure. The term "stereochemically isomeric forms" as used herein defines all the possible stereoisomeric forms of the compounds of formula (I), the pharmaceutically acceptable addition salts thereof, and the pharmaceutically acceptable solvates thereof. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I), the pharmaceutically acceptable addition salts thereof, and the pharmaceutically acceptable solvates thereof substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer. In particular, stereogenic centers may have the R- or S-configuration; substituents on bivalent cyclic (partially) saturated radicals may have either the cis- or trans-configuration.

Compounds having double bonds can have an E (entgegen) or Z (zusammen)-stereochemistry at said double bond. The terms cis, trans, R, S, E and Z are well known to a person skilled in the art.

Some of the compounds of formula (I) may also exist in their tautomeric form. Such forms although not explicitly indicated in the above formula are intended to be included within the scope of the present invention.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula (I)", "the present compounds", "the compounds of the present invention" or any equivalent terms, and similarly, the terms "subgroups of compounds of formula (I)", "subgroups of the present compounds", "subgroups of the compounds of the present invention" or any equivalent terms, are meant to include the compounds of general formula (I), or subgroups of the compounds of general formula (I), as well as their salts, solvates, and stereoisomers.

Whenever mention is made hereinbefore or hereinafter that substituents can be selected each independently out of a list of definitions, such as for example for $R^1$ and $R^{5d}$, any possible combinations are intended to be included that are chemically possible or that lead to molecules of such chemical stability that they can be processed in standard pharmaceutical procedures.

One embodiment of the present invention concerns compounds of formula

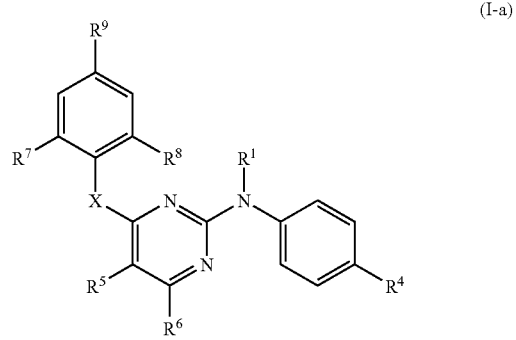

(I-a)

the pharmaceutically acceptable addition salts, the pharmaceutically acceptable solvates, and stereochemically isomeric forms thereof, wherein X, $R^1$, $R^4$, $R^5$, $R^6$, $R^7$, $R^8$ and $R^9$ are as defined above.

In one embodiment, $R^9$ in the compounds of formula (I) or (I-a) is $C_{1-6}$alkyl, $C_{2-6}$alkenyl, or $C_{1-6}$alkynyl, each substituted with cyano. In another embodiment, $R^8$ in the compounds of formula (I) or (I-a) is $C_2$alkyl, $C_2$alkenyl, or $C_2$alkynyl, each substituted with cyano; wherein the cyano in particular is substituted at a carbon atom that is not linked to the phenyl group. In the latter instance, $R^8$ can be represented by a radical -A-CN, wherein A is —$CH_2$—$CH_2$—, —CH=CH—, or —C≡C—.

Particular subgroups of the compounds of formula (I) or (I-a) or any subgroup of compounds of formula (I) or (I-a) specified herein wherein (a) $R^9$ is —$CH_2$—$CH_2$—CN or —CH=CH—CN; or wherein (b) $R^9$ is —CH=CH—CN.

Of particular interest are those compounds of formula (I) as defined herein, or of any of the subgroups thereof, wherein $R^9$ is —CH=CH—, substituted with any of the $C_{2-6}$alkenyl substituents specified above in relation to the definition of $R^9$, or wherein $R^9$ in particular is —CH=CH—CN, and wherein the substituents on the —CH=CH— moiety are in an E-configuration (i.e. the so-called 'E'-isomers). Of special interest are those compounds of formula (I) as defined herein, or of any of the subgroups thereof, wherein $R^9$ is (E) —CH=CH—CN.

Embodiments of the present invention are those compounds of formula (I) or any of the subgroups of compounds of formula (I) wherein $R^1$ is hydrogen.

Further embodiments of the present invention are those compounds of formula (I) or any of the subgroups of compounds of formula (I) wherein
(a) $R^2$, $R^3$, $R^7$ and $R^8$ independently are hydrogen; hydroxy; halo; $C_{1-6}$alkyl; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^{10}$;
(b) $R^2$, $R^3$, $R^7$ and $R^8$ independently are hydrogen; hydroxy; halo; $C_{1-6}$alkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; —C(=O)$R^{10}$;
(c) $R^2$, $R^3$, $R^7$ and $R^8$ independently are hydrogen; hydroxy; halo; $C_{1-6}$alkyl; $C_{1-6}$alkyloxy; cyano; amino; mono- or di($C_{1-6}$alkyl)amino; polyhalo$C_{1-6}$alkyl;
(d) $R^2$, $R^3$, $R^7$ and $R^8$ independently are hydrogen; halo; $C_{1-6}$alkyl; cyano;
(e) $R^2$ and $R^3$ are hydrogen and $R^7$ and $R^8$ independently are hydrogen; halo; cyano.

Embodiments of the present invention are those compounds of formula (I) or any of the subgroups of compounds of formula (I) wherein
(a) $R^4$ and $R^9$ independently are halo; carboxyl; $C_{1-6}$alkyloxycarbonyl; cyano; —C(=O)$R^{10}$; Het; $C_{1-6}$alkyl optionally substituted with cyano, —C(=O)—$R^{10}$, Het; $C_{2-6}$alkenyl optionally substituted with cyano, —C(=O)—$R^{10}$, Het; and wherein each Het in particular is independently selected from thienyl, furanyl, oxazoyl, thiazolyl, optionally substituted with halo, $C_{1-6}$alkyl, cyano; or
(b) $R^4$ and $R^9$ independently are cyano; —C(=O)$R^{10}$; Het; $C_{1-6}$alkyl optionally substituted with cyano, —C(=O)—$R^{10}$, Het; $C_{2-6}$alkenyl optionally substituted with cyano, —C(=O)—$R^{10}$, Het; and wherein each Het in particular is independently thienyl or furanyl, each optionally substituted with cyano, —C(=O)—$R^{10}$; or
(c) $R^4$ and $R^9$ independently are cyano; $C_{1-6}$alkyl substituted with cyano; $C_{2-6}$alkenyl substituted with cyano; or
(d) $R^4$ is cyano; $R^9$ is $C_{2-6}$alkenyl substituted with cyano.

Embodiments of the present invention are those compounds of formula (I) or any of the subgroups of compounds of formula (I) wherein
(a) $R^5$ is $C_{2-6}$alkenyl or $C_{2-6}$alkynyl both substituted with cyano, aminocarbonyl, mono- and di($C_{1-6}$alkyl)aminocarbonyl, aryl, pyridyl, or with one or two $C_{1-6}$alkyloxy groups; Het; —C(=O)NR$^{5a}$R$^{5b}$; —CH(OR$^{5c}$)R$^{5d}$; wherein
  $R^{5a}$ is $C_{1-6}$alkyloxy; $C_{2-6}$alkenyl; $C_{3-7}$cycloalkyl; or $C_{1-6}$alkyl substituted with mono- and di($C_{1-6}$alkyl)amino, $C_{1-6}$alkylcarbonylamino, cyano, aryl, pyridyl, thienyl, tetrahydrofuranyl, morpholinyl, piperazinyl, piperazinyl optionally substituted with $C_{1-6}$alkyl or with hydroxy$C_{1-6}$alkyl; or $R^{5a}$ is $C_{1-6}$alkyl substituted with one or two $C_{1-6}$alkyloxy;
  $R^{5b}$ is hydrogen or $C_{1-6}$alkyl; or
  $R^{5a}$ and $R^{5b}$ taken together with the nitrogen atom to which they are substituted form piperidinyl optionally substituted with aminocarbonyl or hydroxy; piperazinyl optionally substituted with $C_{1-6}$alkyl or 60 hydroxy$C_{1-6}$alkyl;
  $R^{5c}$ is hydrogen;
  $R^{5d}$ is $C_{1-6}$alkyl, $C_{2-6}$alkenyl, aryl, pyridyl, or thiazolyl; or wherein
(b) $R^5$ is $C_{2-6}$alkenyl substituted with cyano, aminocarbonyl, mono- and di($C_{1-6}$alkyl)aminocarbonyl, aryl, or with one or two $C_{1-6}$alkyloxy groups; or $C_{2-6}$alkynyl substituted with pyridyl, or with one or two $C_{1-6}$alkyloxy groups; or $R^5$ is —C(=O)NR$^{5a}$R$^{5b}$; —CH(OR$^{5c}$)R$^{5d}$; wherein
  $R^{5a}$ is $C_{1-6}$alkyloxy; $C_{2-6}$alkenyl; $C_{3-7}$cycloalkyl; or $C_{1-6}$alkyl substituted with mono- and di($C_{1-6}$alkyl)amino, $C_{1-6}$alkylcarbonylamino, cyano, aryl, pyridyl, thienyl, tetrahydrofuranyl, morpholinyl, piperazinyl, piperazinyl optionally substituted with $C_{1-6}$alkyl or with hydroxy$C_{1-6}$alkyl; or $R^{5a}$ is $C_{1-6}$alkyl substituted with one or two $C_{1-6}$alkyloxy;
  $R^{5b}$ is hydrogen or $C_{1-6}$alkyl; or
  $R^{5a}$ and $R^{5b}$ taken together with the nitrogen atom to which they are substituted form piperidinyl optionally substituted with aminocarbonyl or hydroxy; 4-$C_{1-6}$alkyl-piperazinyl; or 4-(hydroxy$C_{1-6}$alkyl)-piperazinyl;
  $R^{5c}$ is hydrogen;
  $R^{5d}$ is $C_{1-6}$alkyl, $C_{2-6}$alkenyl, or thiazolyl.

Embodiments of the present invention are those compounds of formula (I) or any of the subgroups of compounds of formula (I) wherein $R^6$ is methoxymethyl.

Embodiments of the present invention are those compounds of formula (I) or any of the subgroups of compounds of formula (I) wherein each $R^{10}$ independently is $C_{1-6}$alkyl, amino, mono- or di($C_{1-6}$alkyl)amino.

Embodiments of the present invention are those compounds of formula (I) or any of the subgroups of compounds of formula (I) wherein
(a) X is —NR$^1$—, —O—; or
(b) X is —NR$^1$—; or
(c) X is —N($C_{1-6}$alkyl)-; or
(d) X is —NH—; or
(e) X is —NH— or —O—.

Embodiments of the present invention are those compounds of formula (I) or any of the subgroups of compounds of formula (I) wherein each r is 2.

Embodiments of the present invention are those compounds of formula (I) or any of the subgroups of compounds of formula (I) wherein
(a) each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from $C_{1-6}$alkyl, halo, hydroxy, cyano, $C_{1-6}$alkyloxy, $C_{2-6}$alkenyl substituted with halo, hydroxy or with cyano;
(b) each Het independently is pyridyl, thienyl, furanyl, oxazolyl, thiazolyl; which each may optionally be substituted with $C_{1-6}$alkyl, halo;
(c) each Het independently is pyridyl, thienyl, furanyl, oxazolyl, thiazolyl; or
(d) each Het independently is pyridyl, thienyl, furanyl.

Embodiments of the present invention are those compounds of formula (I) or any of the subgroups of compounds of formula (I) wherein each aryl independently is phenyl or phenyl substituted with one, two or three substituents each independently selected from those mentioned above or in particular from:
(a) halo, hydroxy, $C_{1-6}$alkyl, $C_{2-6}$alkenyl, $C_{2-6}$alkynyl, hydroxy$C_{1-6}$alkyl, amino-$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, phenyl$C_{1-6}$alkyloxy, $C_{1-6}$alkyloxycarbonyl, aminosulfonyl, $C_{1-6}$alkylsulfonyl, cyano, nitro, polyhalo$C_{1-6}$alkyloxy, aminocarbonyl, phenyl, or Het; or (b) halo, hydroxy, C$_{1-6}$alkyl, hydroxyC$_{1-6}$alkyl, aminoC$_{1-6}$alkyl, mono or di(C$_{1-6}$alkyl)aminoC$_{1-6}$alkyl, C$_{1-6}$alkyloxy, phenylC$_{1-6}$alkyloxy, C$_{1-6}$alkyloxycarbonyl, C$_{1-6}$alkylsulfonyl, cyano, polyhaloC$_{1-6}$alkyl, aminocarbonyl;

(c) halo, hydroxy, C$_{1-6}$alkyl, hydroxyC$_{1-6}$alkyl, aminoC$_{1-6}$alkyl, C$_{1-6}$alkyloxy, C$_{1-6}$alkylsulfonyl, cyano, nitro, trifluoromethyl;

(d) halo, hydroxy, C$_{1-6}$alkyl, C$_{1-6}$alkyloxy, C$_{1-6}$alkylsulfonyl, cyano, nitro, trifluoromethyl.

Particular subgroups of compounds of formula (I) or (I-a) are those wherein one, several or all of the following limitations apply:

(a) R$^1$ is hydrogen;
(b-1) R$^2$, R$^3$, R$^7$ and R$^8$ independently are hydrogen; halo; C$_{1-6}$alkyl; cyano; or
(b-2) R$^2$ and R$^3$ are hydrogen and R$^6$ and R$^7$ independently are hydrogen; halo; cyano;
(c-1) R$^4$ and R$^9$ independently are cyano; C$_{1-6}$alkyl substituted with cyano; C$_{2-6}$alkenyl substituted with cyano; or
(c-2) R$^4$ is cyano; R$^9$ is C$_{2-6}$alkenyl substituted with cyano.
(d-1) X is —NR$^1$—, —O—; or (d-2) X is —NH—;
(e-1) R$^5$ is C$_{2-6}$alkenyl or C$_{2-6}$alkynyl both substituted with cyano, aminocarbonyl, mono- and di(C$_{1-6}$alkyl)aminocarbonyl, aryl, pyridyl, or with one or two C$_{1-6}$alkyloxy groups; Het; —C(=O)NR$^{5a}$R$^{5b}$; —CH(OR$^{5c}$)R$^{5d}$; wherein
R$^{5a}$ is C$_{1-6}$alkyloxy; C$_{2-6}$alkenyl; C$_{3-7}$cycloalkyl; or C$_{1-6}$alkyl substituted with mono- and di(C$_{1-6}$alkyl)amino, C$_{1-6}$alkylcarbonylamino, cyano, aryl, pyridyl, thienyl, tetrahydrofuranyl, morpholinyl, piperazinyl, piperazinyl optionally substituted with C$_{1-6}$alkyl or with hydroxyC$_{1-6}$alkyl; or R$^{5a}$ is C$_{1-6}$alkyl substituted with one or two C$_{1-6}$alkyloxy;
R$^{5b}$ is hydrogen or C$_{1-6}$alkyl; or
R$^{5a}$ and R$^{5b}$ taken together with the nitrogen atom to which they are substituted form piperidinyl optionally substituted with aminocarbonyl or hydroxy; piperazinyl optionally substituted with C$_{1-6}$alkyl or hydroxyC$_{1-6}$alkyl;
R$^{5c}$ is hydrogen;
R$^{5d}$ is C$_{1-6}$alkyl, C$_{2-6}$alkenyl, aryl, pyridyl, or thiazolyl;
(e-2) R$^5$ is C$_{2-6}$alkenyl substituted with cyano, aminocarbonyl, mono- and di(C$_{1-6}$alkyl)aminocarbonyl, aryl, or with one or two C$_{1-6}$alkyloxy groups; or C$_{2-6}$alkynyl substituted with pyridyl, or with one or two C$_{1-6}$alkyloxy groups; or R$^5$ is —C(=O)NR$^{5a}$R$^{5b}$; —CH(OR$^{5c}$)R$^{5d}$; wherein
R$^{5a}$ is C$_{1-6}$alkyloxy; C$_{2-6}$alkenyl; C$_{3-7}$cycloalkyl; or C$_{1-6}$alkyl substituted with mono- and di(C$_{1-6}$alkyl)amino, C$_{1-6}$alkylcarbonylamino, cyano, aryl, pyridyl, thienyl, tetrahydrofuranyl, morpholinyl, piperazinyl, piperazinyl optionally substituted with C$_{1-6}$alkyl or with hydroxyC$_{1-6}$alkyl; or R$^{5a}$ is C$_{1-6}$alkyl substituted with one or two C$_{1-6}$alkyloxy;
R$^{5b}$ is hydrogen or C$_{1-6}$alkyl; or
R$^{5a}$ and R$^{5b}$ taken together with the nitrogen atom to which they are substituted form piperidinyl optionally substituted with aminocarbonyl or hydroxy; 4-C$_{1-6}$alkyl-piperazinyl; or 4-(hydroxyC$_{1-6}$alkyl)-piperazinyl;
R$^{5c}$ is hydrogen;
R$^{5d}$ is C$_{1-6}$alkyl, C$_{2-6}$alkenyl, or thiazolyl;
(f) each aryl independently is phenyl or phenyl substituted with one, two, or three substituents each independently selected from (f-1) halo, hydroxy, C$_{1-6}$alkyl, hydroxyC$_{1-6}$alkyl, aminoC$_{1-6}$alkyl, mono or di(C$_{1-6}$alkyl)aminoC$_{1-6}$alkyl, C$_{1-6}$alkylcarbonyl, C$_{3-7}$cycloalkyl, C$_{1-6}$alkyloxy, C$_{1-6}$alkyloxycarbonyl, C$_{1-6}$alkylsulfonyl, cyano, nitro, trifluoromethyl, aminocarbonyl;

(f-2) halo, hydroxy, C$_{1-6}$alkyl, hydroxyC$_{1-6}$alkyl, aminoC$_{1-6}$alkyl, mono or di(C$_{1-6}$alkyl)-aminoC$_{1-6}$alkyl, C$_{1-6}$alkyloxy, phenylC$_{1-6}$alkyloxy, C$_{1-6}$alkyloxycarbonyl, C$_{1-6}$alkylsulfonyl, cyano, polyhaloC$_{1-6}$alkyl, aminocarbonyl;

(f-3) halo, hydroxy, C$_{1-6}$alkyl, hydroxyC$_{1-6}$alkyl, aminoC$_{1-6}$alkyl, C$_{1-6}$alkyloxy, C$_{1-6}$alkylsulfonyl, cyano, nitro, trifluoromethyl;

(f-4) halo, hydroxy, C$_{1-6}$alkyl, C$_{1-6}$alkyloxy, C$_{1-6}$alkylsulfonyl, cyano, nitro, trifluoromethyl.

The compounds of formula (I) can be prepared by reacting an intermediate of formula (II) wherein W represents a suitable leaving group, such as for example halogen, e.g. chloro, bromo or a tosyl, mesyl, and the like groups, with an intermediate of formula (III).

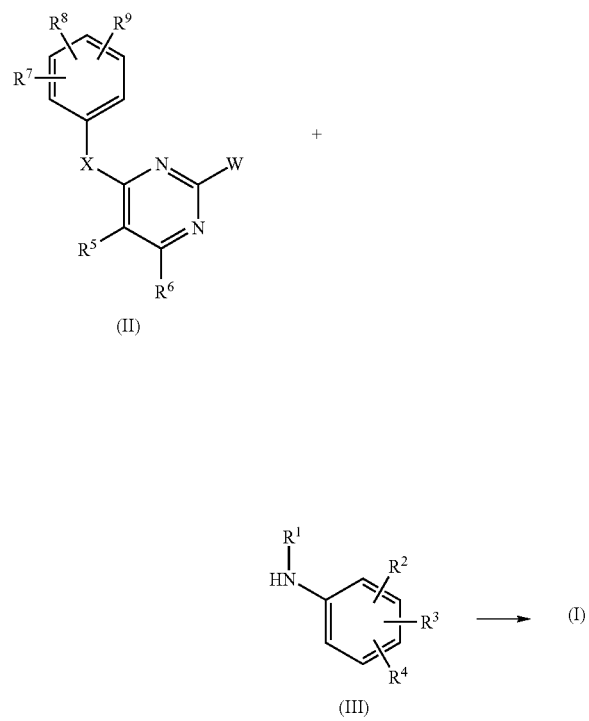

The reaction of (II) with (III) is usually conducted in the presence of a suitable solvent. Suitable solvents are for example an alcohol, such as for example ethanol, 2-propanol; a dipolar aprotic solvent such as acetonitrile, N,N-dimethylformamide, N,N-dimethyl-acetamide, 1-methyl-2-pyrrolidinone; an ether such as tetrahydrofuran, 1,4-dioxane, propylene glycol monomethylether. The reaction can be done under acid conditions obtained by adding amounts of a suitable acid such as for example camphor sulfonic acid, or by using acid solvents, e.g. hydrochloric acid dissolved in an alkanol such as 1- or 2-propanol.

The compounds of formula (I) can also be prepared by forming the X linkage by either reacting (IV-a) with (V-a) or (IV-b) with (V-b) as outlined in the following scheme.

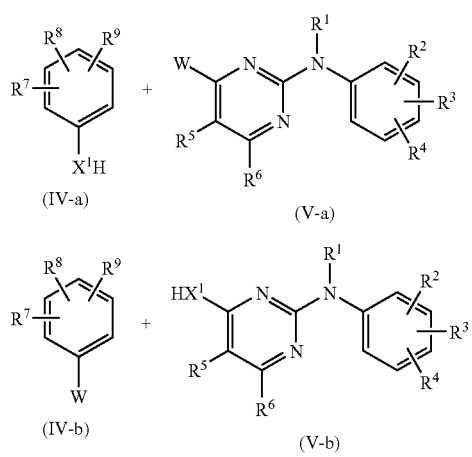

(IV-a)  (V-a)  (I-a)

(IV-b)  (V-b)

In this reaction scheme W represents an appropriate leaving group, which in particular is as specified above. The leaving group W in (V-a) may also be introduced in situ, e.g. by converting the corresponding hydroxy function into a leaving group for example by $POCl_3$. $X^1$ represents $-NR^1-$, $-O-$, $-S-$. Where $X^1$ is $NR^1$, the above reactions preferably are conducted in the presence of a tertiary amine base, e.g. triethylamine. Where $X^1$ represents O or S, the above reactions are conducted in the presence of a base such as for example $K_2CO_3$ or potassium t-butoxide (KOt-Bu).

The compounds of formula (I) wherein $R^5$ is a group Het, said compounds being represented by formula (I-b), can be prepared by a Suzuki reaction, i.e. by reacting a 6-halopyrimidine derivative (VI) with a heterocyclyl boric acid Het-B $(OH)_2$ or heterocyclyl boric acid ester (in particular an alkyl ester such as methyl or ethyl ester) in the presence of a palladium catalyst, in particular $Pd(PPh_3)_4$.

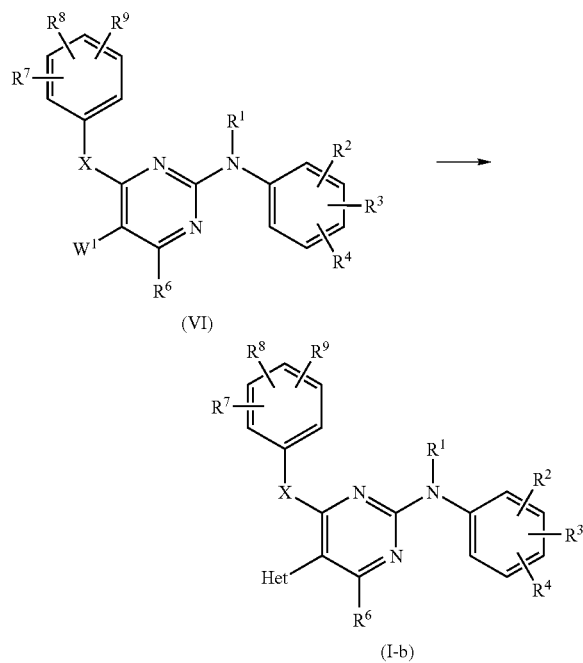

(VI)

(I-b)

$W^1$ is halo (such as I, Br or Cl) or a pseudohalo group (such as triflate).

The compounds of formula (I) wherein $R^5$ is a group $-C(=O)NR^{5a}R^{5b}$, said compounds being represented by formula (I-c), can be prepared by reacting a carboxylic acid or an active form thereof (VII) with an amine (VIII), in an amide bond forming reaction.

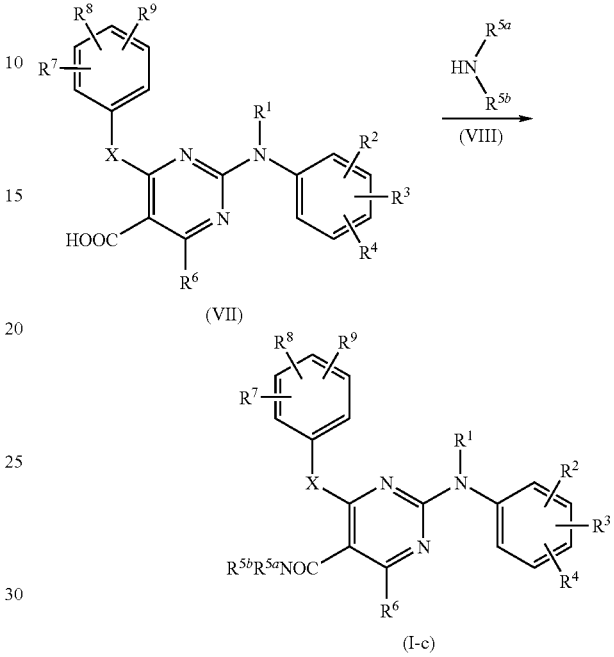

(VII)

(I-c)

The amide bond forming reaction may be performed by reacting the starting materials in the presence of a coupling agent or by converting the carboxyl group in (VII) into an activated form such as a carboxylic acid halide such as an acid chloride or bromide, a carboxylic acid azide, a mixed carbonic-carboxylic acid anhydride (e.g. by reaction with isobutyl chloroformate), an active ester (p-nitrophenyl ester, pentachloro-phenylester, N-hydroxysuccinic imido ester). The amines (VIII) may also be reacted with carboxylic acid lower alkyl esters, in particular the methyl or ethyl esters. Examples of coupling agents include the carbodiimides (dicyclohexylcarbodiimide, diisopropylcarbodiimide, or water-soluble carbodiimide such as N-ethyl-N'-[(3-dimethylamino)propyl] carbodiimide) or carbonyldiimidazoles. Some of these methods can be enhanced by adding suitable catalysts, e.g. in the carbodiimide method by adding 1-hydroxybenzotriazole or 4-dimethylaminopyridine (4-DMAP).

The amide bond forming reactions preferably are conducted in an inert solvent, such as halogenated hydrocarbons, e.g. dichloromethane, chloroform, dipolar aprotic solvents such as acetonitrile, dimethylformamide, dimethylacetamide, ethers such as tetrahydrofuran. In many instances the coupling reactions are done in the presence of a suitable base such as a tertiary amine, e.g. triethylamine, diisopropylethylamine (DIPEA), N-methylmorpholine, N-methylpyrrolidine, or 4-DMAP.

The compounds of formula (I) wherein $R^5$ is $-CH_2-NR^{5e}R^{5f}$, said compounds being represented by formula (I-d), can be prepared by a reductive amination reaction starting from the aldehydes (IX) with an amine (XI). The reductive amination may be conducted with hydrogen in the presence of a noble metal catalyst such as Pt or Pd, or with a cyanoborohydride. These compounds can also be prepared by an N-alkylation reaction starting from intermediates (X), wherein W is as specified above and in particular is chloro or bromo, with an amine (XI).

as an alkali metal, in particular Li, Na or K, or a magnesium derivative such as a Grignard type of reagent (M-$R^5$ is halo-Mg—$R^5$). These reactions typically are conducted in a reaction-inert solvent such as an ether (tetrahydrofuran, diethyl-ether, dioxane) or a halogenated hydrocarbon ($CH_2Cl_2$, $CHCl_3$).

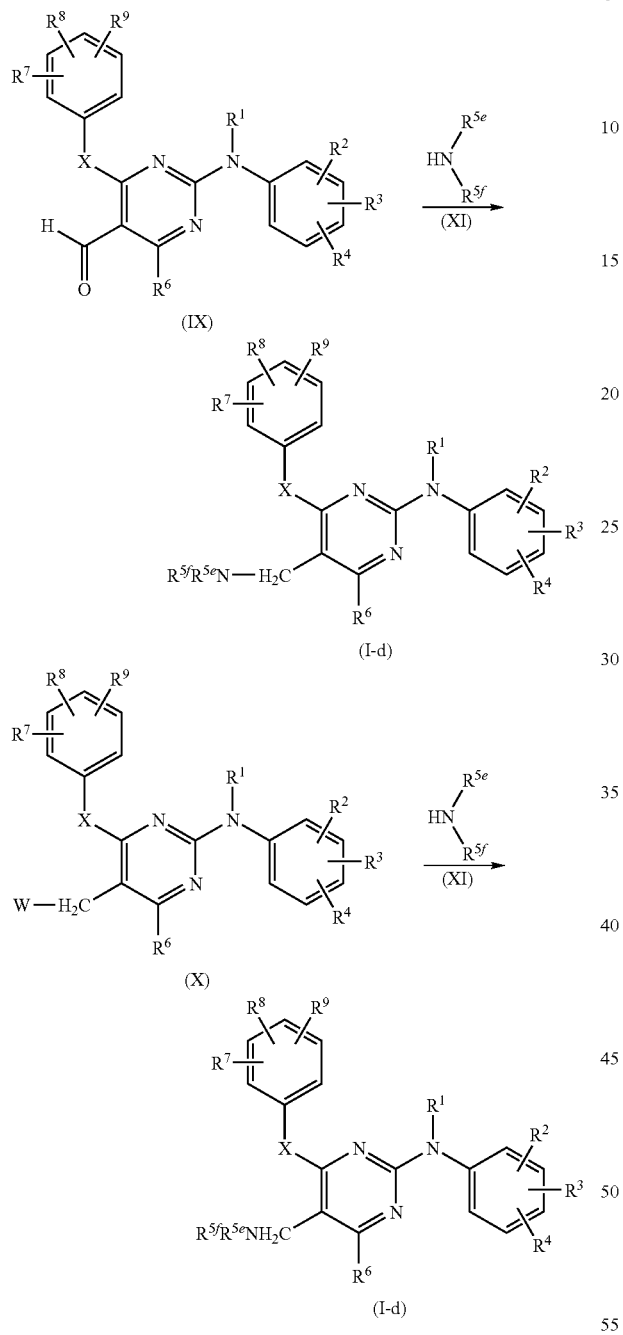

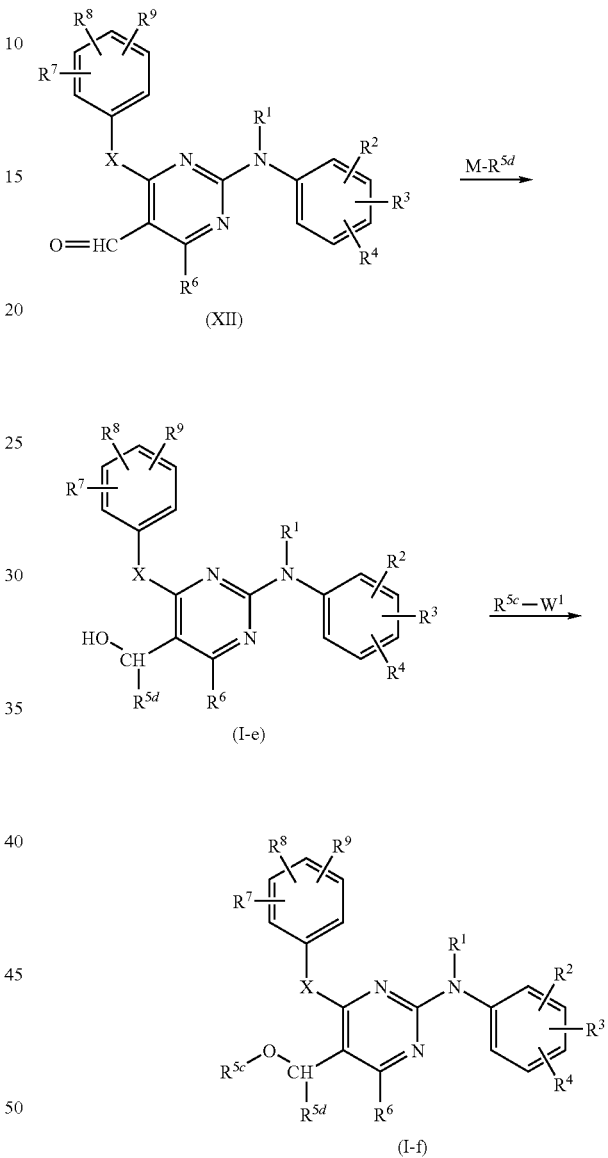

The compounds of formula (I-f), which are compounds of formula (I) wherein $R^5$ is —CH(O$R^{5c}$)$R^{5d}$, can be prepared by reacting a pyrimidine aldehyde of formula (XII) with an organo-metal compound (M-$R^{5d}$). The thus obtained compounds of formula (I-e) can be converted to the corresponding compounds of formula (I-f), which are corresponding compounds wherein $R^{5c}$ is other than hydrogen. The group $R^{5c}$ can be introduced by an ether forming reaction such as an O-alkylation reaction with a reagent $W^1$—$R^{5c}$, wherein $W^1$ is a leaving group such as halo, in particular chloro, bromo or iodo, or a sulfate or azide group. M in M-$R^{5d}$ is a metal such The compounds of formula (I-g), which are compounds of formula (I) wherein $R^5$ is $R^{5e}$, the latter being substituted $C_{2-6}$alkenyl or $C_{2-6}$alkynyl, can be prepared by reacting an intermediate (VI), which is as specified above, with an organometallic or organoboric alkene or alkyne derivative $R^{5e}$-$M^1$. Where $M^1$ represents boronic acid or a boronic acid ester, this reaction is a Suzuki type of reaction. Where $M^1$ is a trialkylstannane, in particular a tributyl stannane, this reaction is a Stille reaction. Another type of reaction that can be used is the Heck reaction where the alkene is reacted with (VI) in the presence of a palladium catalyst. Other Pd-catalysed cross couplings of heteroaryl halides that can be used are the Kumada coupling, Hiyama coupling, and the Sonogashira coupling.

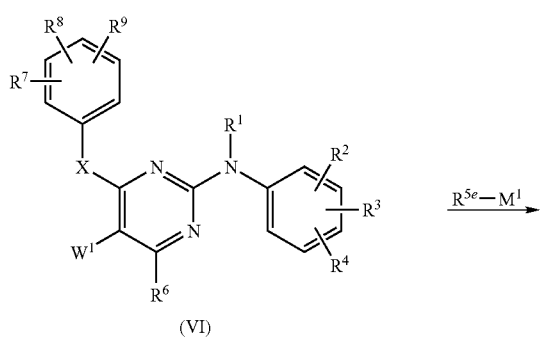

(VI)

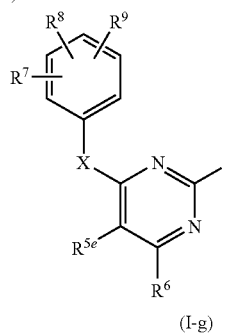

(I-g)

Some of the intermediates and starting materials are known compounds and may be commercially available or may be prepared according to art-known procedures.

Intermediates of formula (II) can be prepared by reacting an intermediate of formula (XIII) wherein each W is as defined hereinabove, with an intermediate of formula (XIV) in a suitable solvent, such as for example tetrahydrofuran, usually in the presence of a suitable base, such as for example $Na_2CO_3$. $X^1$ in the following schemes represents —$NR^1$—, —O—, or —S—.

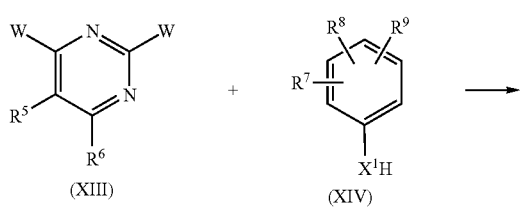

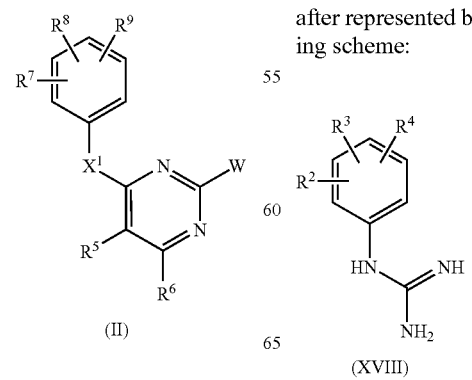

(II)

The intermediates (V-a) and (V-b) can be prepared as follows:

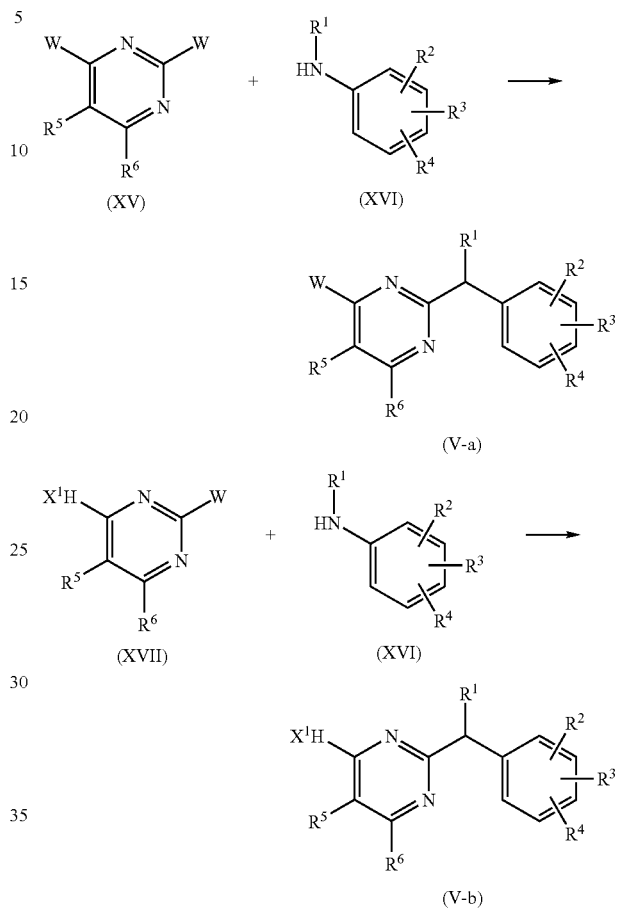

Pyrimidine derivative (XV), for example 2,4-dichloropyrimidine is reacted with aniline derivative (XVI) yielding (V-a), or similarly, pyrimidine derivative (XVII) is reacted with (XVI) yielding (V-b). Preferably the $X^1$ group in (XVI) is protected, e.g. in case of $X^1$ being an amine by an acetyl, butyloxycarbonyl, or benzyl group, or in case of $X^1$ being O by a methyl, benzyl or t.Bu group. After reaction with (XVI), the protecting group is removed and (V-b) is obtained. The reactions of (XV) or (XVII) with (XVI) are conducted in a reaction inert solvent, usually in the presence of a base.

The intermediates of formula (VI) wherein X is NH, hereafter represented by (VI-a), can be prepared as in the following scheme:

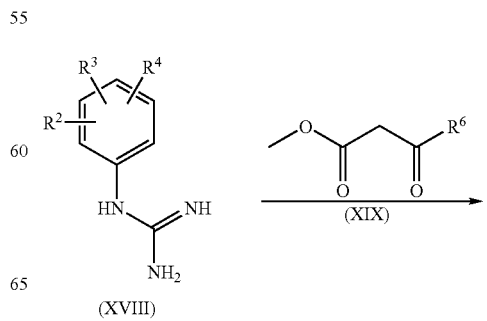

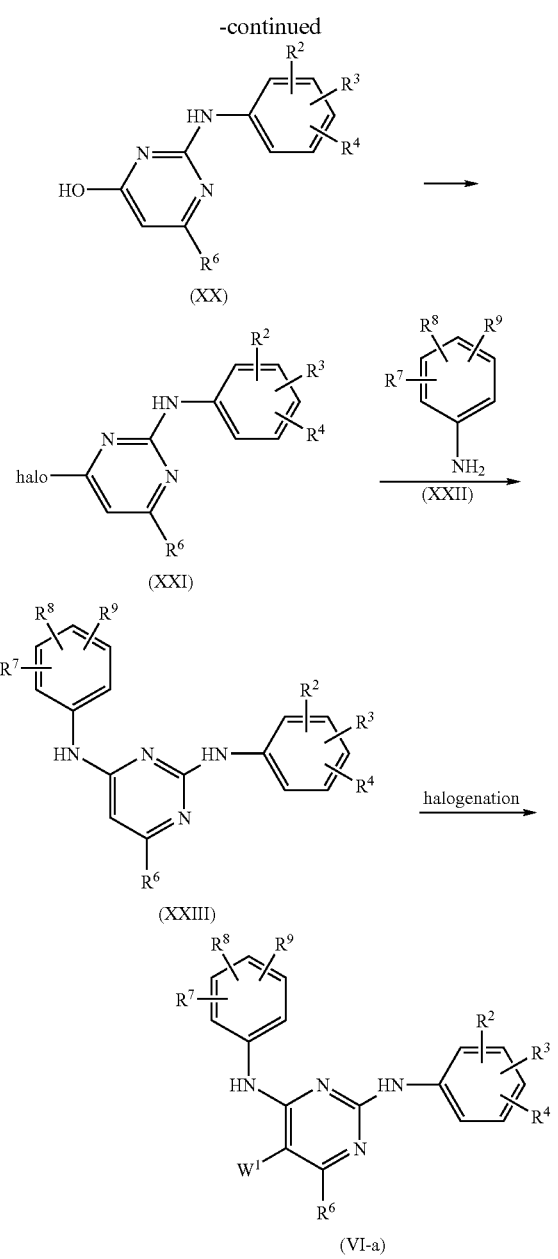

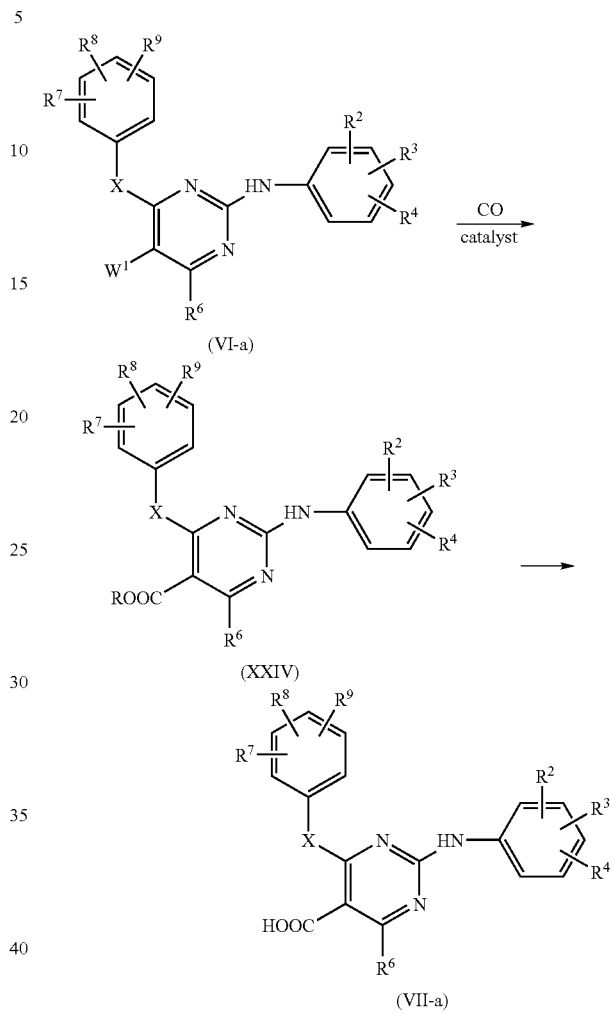

(i.e. bis(triphenylphosphine)palladium(II) chloride) in an alcohol in the presence of a base. Basic hydrolysis of (XXIV) yields acids (VII-a).

In a first step, an arylguanidine (XVIII) is condensed with an acetoacetic acid (XIX), e.g. with 4-methoxyacetoacetic acid. The thus obtained hydroxypyrimidine (XX) is converted to the corresponding halopyrimidine (XXI) using a halogenating agent such as POCl$_3$. The halo group is substituted by an aniline derivative (XXII) to pyrimidine derivative (XXIII). The latter is halogenated, yielding an intermediate (VI). The halogenation of (XXIII) can be done with iodine chloride (ICl), in which case W$^1$ in (VI-a) is iodo. Intermediates of formula (VI) wherein X is NR$^1$ other than NH can be obtained through alkylation or acylation of (VI-a) or one of its precursors. Reaction of (XXI) with the phenol or mercapto analogue of aniline (XXII) yields analogues of intermediates (VI-a) wherein X is O or S.

Intermediates (VI-a) can be converted to the corresponding carboxylic acid esters (XXIV) using carbon monoxide in the presence of a catalyst such as a Pd catalyst, e.g. PdCl$_2$(PPh$_3$)$_2$ Compounds of formula (I) wherein R$^2$, R$^3$, R$^7$, or R$^8$ is hydrogen, can be converted into a compound of formula (I) wherein R$^2$, R$^3$, R$^7$, or R$^8$ is halo, by reaction with a suitable halo-introducing agent, such as for example N-chlorosuccinimide or N-bromosuccinimide, in the presence of a suitable solvent, such as for example acetic acid. Compounds of formula (I) wherein R$^1$ represents C$_{1-6}$alkyloxycarbonyl, can be converted into a compound of formula (I) wherein R$^1$ represents hydrogen, by reaction with a suitable base, such as for example sodium hydroxide or methoxide. Where R$^1$ is t.butyloxycarbonyl, the corresponding compounds wherein R$^1$ is hydrogen can be made by treatment with trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically. An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

The compounds of formula (I) show antiretroviral properties (reverse transcriptase inhibiting properties), in particular against HIV, the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever-decreasing number of T-4 cells, which moreover behave abnormally. Hence, the immunological defence system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against drug- and multidrug-resistant HIV strains, in particular multidrug resistant HIV strains, more in particular the present compounds show activity against HIV strains that have acquired resistance to one or more art-known non-nucleoside reverse transcriptase inhibitors, in particular those that have been approved for therapy such as efavirenz, delavirdine, and nevirapine.

Due to their antiretroviral properties, particularly their anti-HIV properties, the compounds of formula (I), the pharmaceutically acceptable addition salts thereof, and the stereoisomeric forms thereof, are useful in the treatment of individuals infected by HIV and for the prophylaxis of these infections. The compounds of the present invention may also find use in the treatment of warm-blooded animals infected with viruses whose existence is mediated by, or depends upon, the enzyme reverse transcriptase. Conditions that may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In a further aspect this invention provides a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a pharmaceutically acceptable addition salt, a pharmaceutically acceptable solvate thereof, or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared wherein the carrier comprises a saline solution, a glucose solution, or a mixture of saline and glucose solution. Injectable suspensions may also be prepared in which case appropriate liquid carriers, suspending agents and the like may be employed. Also included are solid form preparations that can be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126, 443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), e.g. NcRTI-1 and the like; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232,632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors, which comprise fusion inhibitors (e.g. enfuvirtide (T-20)), attachment inhibitors and co-receptor inhibitors, the latter comprise the CCR5 antagonists (e.g. ancriviroc, CCR5mAb004, maraviroc (UK-427,857), PRO-140, TAK-220, TAK-652, vicriviroc (SCH-D, SCH-417,690)) and CXR4 antagonists (e.g. AMD-070, KRH-27315), examples of entry inhibitors are PRO-542, TNX-355, BMS-488,043, BlockAide/CR™, FP 21399, hNM01, nonakine, VGV-1; a maturation inhibitor for example is PA-457; inhibitors of the viral integrase e.g. raltegravir (MK-0518), elvitegravir (JTK-303, GS-9137), BMS-538,158; ribozymes; immunomodulators; monoclonal antibodies; gene therapy; vaccines; siRNAs; antisense RNAs; microbicides; Zinc-finger inhibitors.

The combinations may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) with antibiotics (e.g. pentamidine isothiorate) cytokines (e.g. Th2), modulators of cytokines, chemokines or modulators of chemokines, chemokine receptors (e.g. CCR5, CXCR4), modulators chemokine receptors, or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

Although the present invention focuses on the use of the present compounds for preventing or treating HIV infections, the present compounds may also be used as inhibitory agents for other viruses that depend on reverse transcriptases for multiplication.

The following examples are intended to illustrate the present invention and not to limit its scope thereto.

EXAMPLE 1

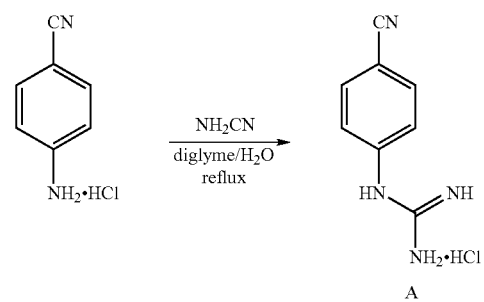

A mixture of 4-cyanoaniline (0.420 mol) in 2-methoxyethyl ether (250 ml) was stirred at 100° C. for 30 min. Then a mixture of cyanamide (0.630 mol) in water (30 ml) was added portion wise during 45 min. After stirring 24 hours at 100° C., cyanamide (0.210 mol) was added again. The mixture was then stirred at 100° C. for an additional 48 hours and subsequently evaporated until dryness. The residue crystallized from acetone yielded 70.5 g of A (85% yield, melting point: 225° C.).

To a solution of intermediate A (0.0102 mol), prepared as in example 1, in ethanol (25 ml) was added sodium ethoxide (21%) (0.0153 mol, 1.5 eq.) followed by methyl 4-methoxyacetoacetate (0.0102 mol, 1 eq.). The resulting mixture was stirred at reflux for 6 hours and then allowed to cool down to room temperature. Water was added and the mixture acidified with acetic acid (until pH=6). The resulting precipitate was filtered to give 1.5 g of intermediate B (57% yield).

A mixture of B (0.0056 mol) and phosphorus oxychloride (10 ml) was stirred at reflux for 30 min. After cooling down, phosphorus oxychloride was evaporated. Water and K$_2$CO$_3$ 10% were added and the mixture was extracted with CH$_2$Cl$_2$. The organic layer was dried over magnesium sulfate, filtered and the solvent evaporated to give 1.51 g of C (97% yield).

A mixture of intermediate C (0.00182 mol) and 3-(4-amino-3,5-dimethylphenyl)-acrylonitrile (0.00182 mol) were heated at fusion temperature for 5 minutes, then poured in a mixture of water and K$_2$CO$_3$ 10%. The resulting mixture was extracted with CH$_2$Cl$_2$. The organic layer was dried over magnesium sulfate, filtered and the solvent evaporated. The residue was purified by column chromatography over silica gel (35-70 μm; eluent: CH₂Cl₂/methanol 97:3). The pure fractions were collected and the solvent evaporated to give 0.34 g of intermediate D (46% yield, melting point: 115° C.).

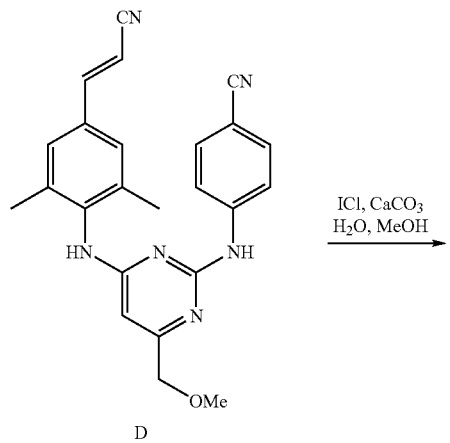

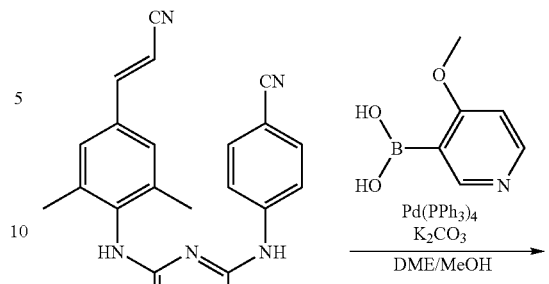

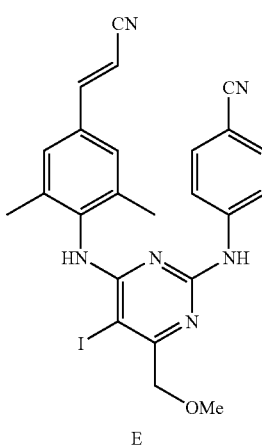

To a solution of intermediate D (15.3 g, 37.2 mmol) in methanol (500 ml) and water (75 ml) was added CaCO₃ (44.7 mmol, 1.2 eq.) followed by iodine chloride drop wise (74.5 mmol, 2 eq.). The resulting mixture was stirred at room temperature for 72 hours. A saturated aqueous solution of Na₂S₂O₃ was added and the mixture was stirred for 30 min. Methanol was evaporated and the resulting mixture was extracted with ethyl acetate. The combined organic layers were dried over MgSO₄ and filtered. The solvent was evaporated and the resulting mixture E was used without purification in the next reactions (20.6 g, 100% yield).

To a solution of intermediate E (0.25 g, 0.47 mmol) in a 5:1 mixture of 1,2-dimethoxyethane/methanol (18 ml), was added successively 4-methoxy-3-pyridinylboronic acid (1.4 mmol, 3 eq.), tetrakis(triphenylphosphine)palladium(0) (Pd (PPh₃)₄) (0.094 mmol, 0.2 eq.), and a 2 N K₂CO₃ solution (2.4 mmol, 5 eq.). The resulting mixture was stirred at reflux overnight. A 10% K₂CO₃ solution was added and the mixture was filtered over a Celite pad and washed with CH₂Cl₂. The residue was extracted with CH₂Cl₂/tetrahydrofuran. The combined organic layers were dried over MgSO₄ and filtered. The solvent was evaporated and the resulting mixture was purified by column chromatography (5 μm, eluent: CH₂Cl₂/methanol/NH₄OH 99:1:0.1 to 95:5:0.5) to give 0.151 g of compound 1 (62% yield, melting point 120° C.).

In this and the following tables, the bond marked ✦ represents the bond linking the radical to the remainder of the molecule. Me and Et refer to methyl and ethyl respectively.

TABLE 1
| Compound No. | Het | Phys. data, stereochemistry and yield |
|---|---|---|
| 1 | 4-methoxypyridin-3-yl | E/Z 85/15<br>62% yield<br>mp: 120° C. |
| 2 | pyridin-3-yl | E/Z 75/25<br>35% yield<br>mp: 216° C. |
| 3 | pyridin-4-yl | E/Z 80/20<br>55% yield<br>mp: 172° C. |
| 4 | thiophen-2-yl | E/Z 80/20<br>48% yield<br>mp: 130° C. |
| 5 | thiophen-3-yl | 47% yield<br>mp: 125° C. |
| 6 | furan-2-yl | E/Z 75/25<br>42% yield<br>mp: 105° C. |
| 7 | furan-3-yl | E/Z 86/14<br>56% yield<br>mp: 122° C. |
EXAMPLE 2
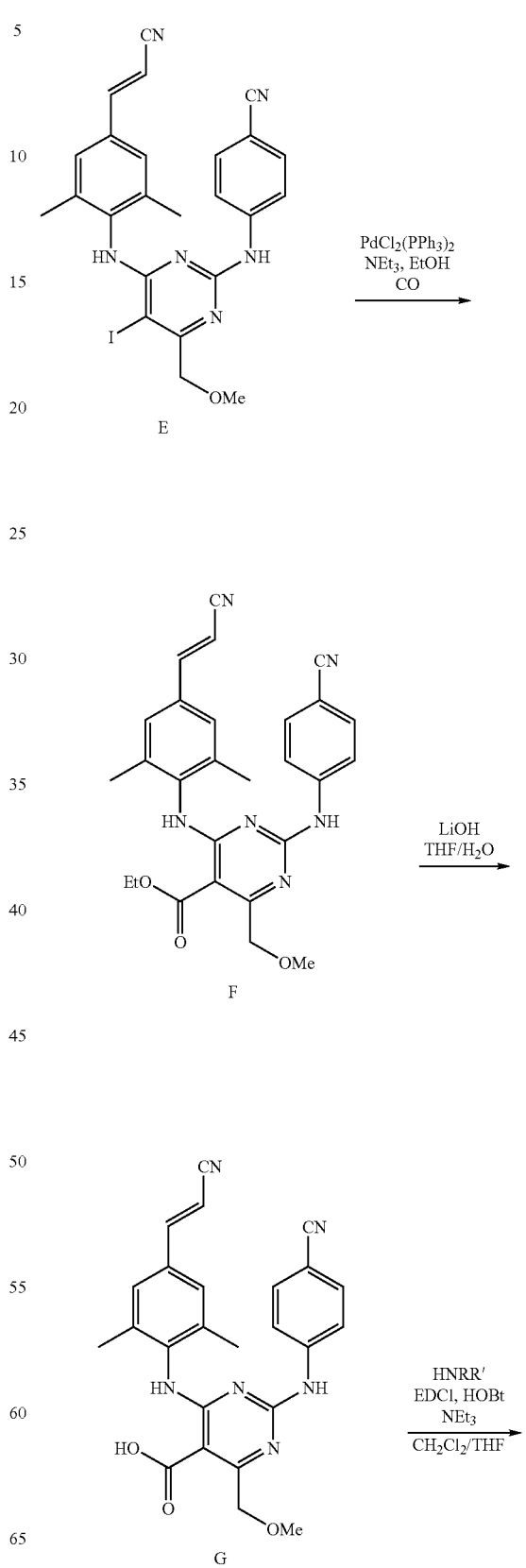

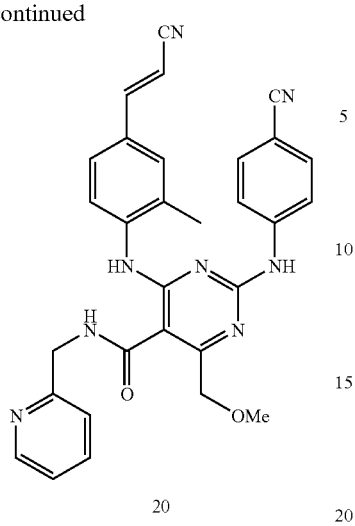

20

To a solution of intermediate E (14 g, 0.026 mol) in ethanol (100 ml) were added bis(triphenylphosphine)palladium(II) chloride ($PdCl_2(PPh_3)_2$) (0.00522 mol, 0.2 eq.) and triethylamine (0.0112 mol, 4.3 eq.). The whole mixture was heated at 110° C. under a 25 bar pressure of carbon monoxide for 48 hours. The resulting mixture was subsequently filtered over a celite pad, rinsed with tetrahydrofuran. After evaporation of the solvent, the resulting mixture was purified by column chromatography (20-45 µm, eluent: $CH_2Cl_2$/methanol 99:1) to give 10.65 g of intermediate F (85% yield, melting point: 156° C.).

To a solution of F (5.4 g, 0.0112 mol) in a mixture tetrahydrofuran/$H_2O$ (50 ml/15 ml), was added LiOH monohydrate (0.0559 mol, 5 eq.). The resulting mixture was stirred at room temperature overnight. Tetrahydrofuran was then evaporated, water added and the mixture acidified to pH 1 with a 3 N HCl solution. The precipitate was then filtered and dried under vacuum to give 4.55 g of intermediate G (89% yield, melting point: 220° C.) used in the next step without further purification.

To a solution of intermediate G (0.15 g, 0.33 mmol) in a 1:1 mixture tetrahydrofuran/$CH_2Cl_2$ (5 ml), was added successively 2-(aminomethyl)pyridine (0.5 mmol, 1.5 eq.), 1-hydroxybenzotriazole (0.5 mmol, 1.5 eq.), 1-(3-dimethylaminopropyl)-3-ethylcarbodiimide hydrochloride (EDCI) (0.5 mmol, 1.5 eq.) and triethylamine (0.5 mmol, 1.5 eq.). The resulting mixture was stirred at room temperature overnight. A 10% $K_2CO_3$ solution was added to the mixture and the residue was extracted with $CH_2Cl_2$. The combined organic layers were dried over $MgSO_4$ and filtered. The solvent was evaporated and the resulting mixture (0.345 g) was crystallized from iso-propanol giving 0.087 g of compound 20 (48% yield).

TABLE 2

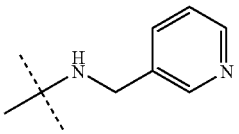

| Compound No. | —NR$^{5a}$R$^{5b}$ | Phys. data, stereochemistry and yield |
|---|---|---|
| 8 | 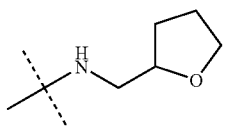 | E/Z 90/10<br>68% yield<br>mp > 250° C. |
| 9 | 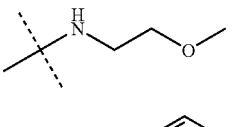 | E/Z 93/7<br>59% yield<br>mp: 200° C. |
| 10 | 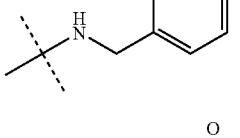 | E/Z 88/12<br>40% yield<br>mp: 181° C. |
| 11 | 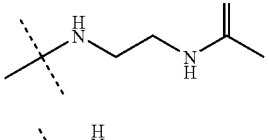 | E/Z 88/12<br>82% yield<br>mp > 250° C. |
| 12 | 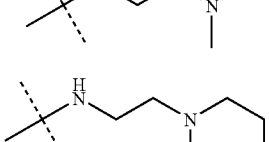 | E/Z 85/15<br>41% yield<br>mp: — |
| 13 | 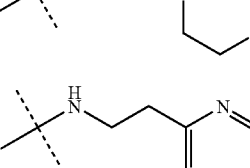 | E<br>39% yield<br>mp: 171° C. |
| 14 | 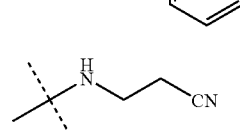 | E/Z 88/12<br>41% yield<br>mp: 178° C. |
| 15 |  | E<br>45% yield<br>mp: 163° C. |
| 16 | | E/Z 88/12<br>64% yield<br>mp: 217° C. |

TABLE 2-continued

[Structure: pyrimidine core with cyanovinyl-dimethylphenyl-NH and 4-cyanophenyl-NH substituents, R^(5a)R^(Rb)N-C(O)- group, and CH2-OMe group]

| Compound No. | —NR^(5a)R^(5b) | Phys. data, stereochemistry and yield |
|---|---|---|
| 17 | piperazine-N-CH2CH2OH | E, 60% yield, mp: 227° C. |
| 18 | NH-CH2-(2-thienyl) | E/Z 88/12, 67% yield, mp: 223° C. |
| 19 | NH-CH2-CH(OMe)2 | E, 38% yield, mp: 193° C. |
| 20 | NH-CH2-(2-pyridyl) | E, 48% yield, mp: 216° C. |
| 21 | N(CH3)-CH2CH2-N(CH3)2 | E/Z 93/7, 67% yield, mp: 126° C. |
| 22 | piperidinyl-3-carboxamide | E/Z 80/20, 56% yield, mp: 181° C. |
| 23 | NH-cyclopropyl | E, 59% yield, mp: 220° C. |
| 24 | NH-allyl | E, 55% yield, mp: 192° C. |
| 25 | N(CH3)(OMe) | E/Z 80/20, 36% yield, mp: 248° C. |
| 26 | 4-methylpiperazin-1-yl | E/Z 80/20, 11% yield, mp: — |
| 27 | 4-hydroxypiperidin-1-yl | E/Z 83/17, 14% yield, mp: — |
| 28 | morpholin-4-yl | E/Z 80/20, 49% yield, mp: — |
| 29 | NH-CH2CH2-(4-SO2NH2-phenyl) | E/Z 75/25, 53% yield, mp: — |
| 30 | NH-CH2CH2-(2-thienyl) | E, 42% yield, mp: 150° C. |

Intermediates H and I were prepared following the same procedures as described in example 1. Compounds 31 and 32 were prepared following the procedures as described in example 2:

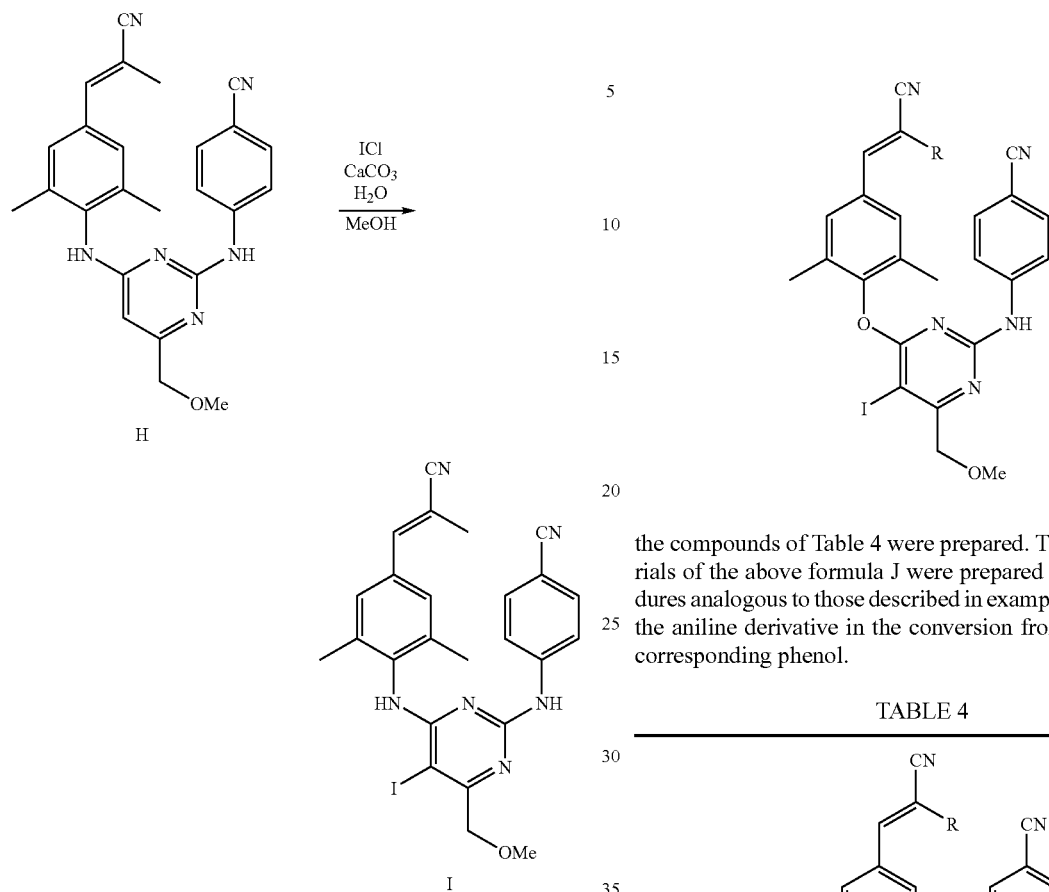

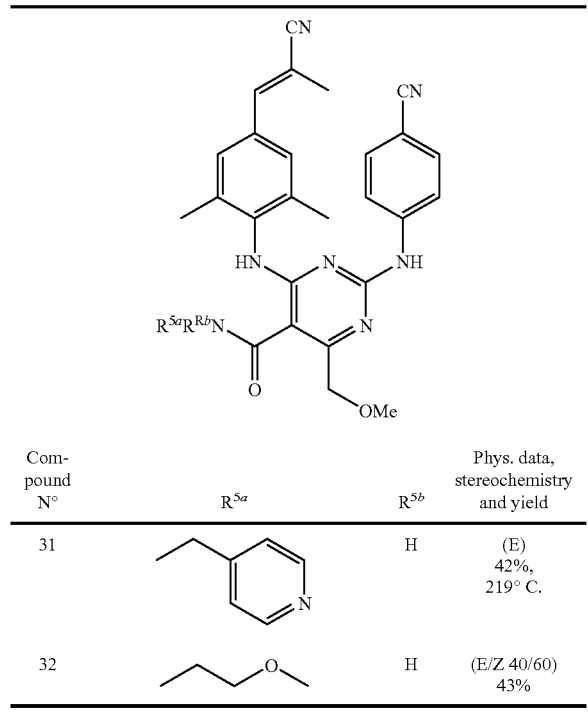

TABLE 3

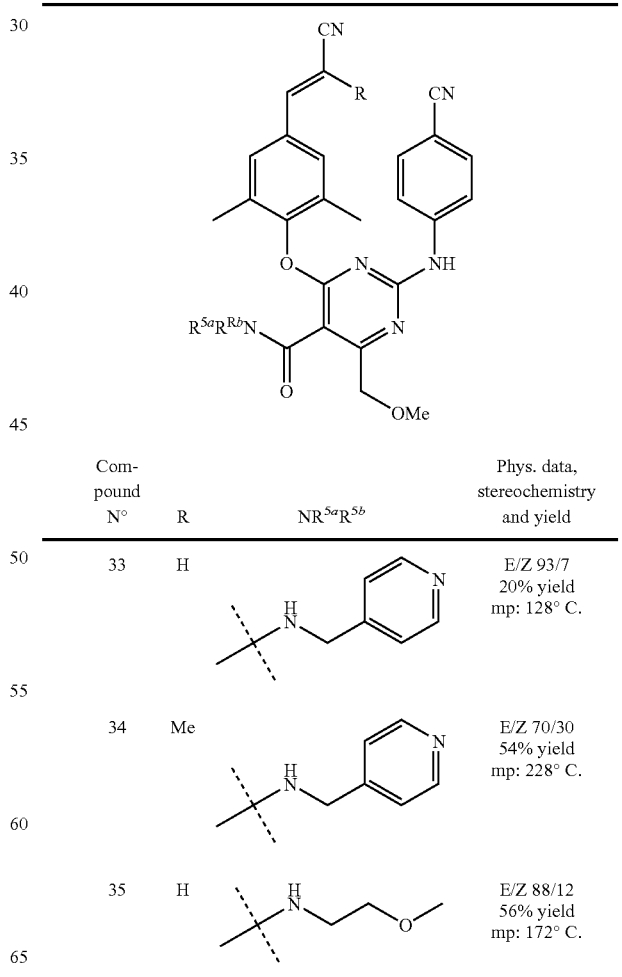

| Compound N° | R5a | R5b | Phys. data, stereochemistry and yield |
|---|---|---|---|
| 31 | ![4-pyridyl-CH2CH2-] | H | (E) 42%, 219° C. |
| 32 | ![CH3OCH2CH2CH2-] | H | (E/Z 40/60) 43% |

Following the same procedures, but starting from the compounds of Table 4 were prepared. The starting materials of the above formula J were prepared following procedures analogous to those described in example 1 but replacing the aniline derivative in the conversion from C to D by the corresponding phenol.

TABLE 4

| Compound N° | R | NR5aR5b | Phys. data, stereochemistry and yield |
|---|---|---|---|
| 33 | H | ![4-pyridyl-CH2-NH-] | E/Z 93/7 20% yield mp: 128° C. |
| 34 | Me | ![4-pyridyl-CH2-NH-] | E/Z 70/30 54% yield mp: 228° C. |
| 35 | H | ![CH3O-CH2CH2-NH-] | E/Z 88/12 56% yield mp: 172° C. |

EXAMPLE 3

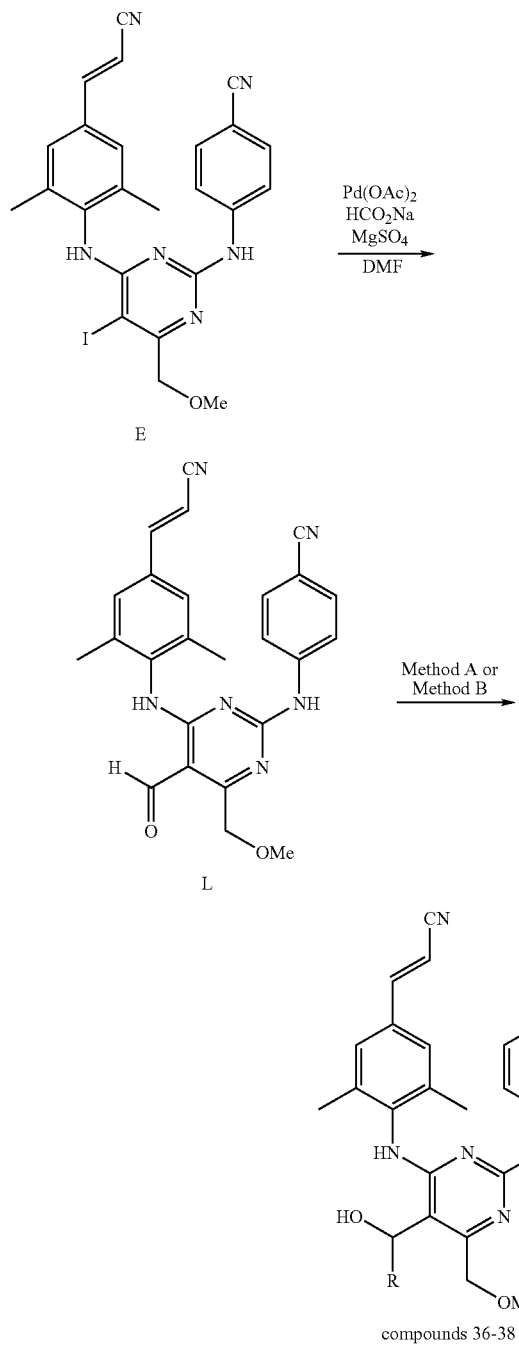

compounds 36-38

A mixture of intermediate E (0.00372 mol), palladium acetate (0.000746 mol, 0.2 eq), sodium formate (0.0111 mol, 3 eq) and some MgSO$_4$ in 50 ml of dimethyl formamide was stirred at 100° C. under a 30 bar pressure of carbon monoxide overnight. The mixture was poured in water. The precipitate was filtered off and dried. The crude product was purified by chromatography over silica gel (eluent: CH$_2$Cl$_2$/methanol/ NH$_4$OH: 99/1/0.1; 15-40 μM). The pure fractions were collected and the solvent was evaporated. Yield: 0.410 g (25%) of intermediate L.

Method A

To a mixture of intermediate L (0.0008 mol) in 15 ml of tetrahydrofuran was added methylmagnesium chloride (0.00279 mol, 3.5 eq) at −78° C., under a nitrogen atmosphere. The mixture was stirred two hours at −78° C., then overnight at room temperature. The reaction mixture was poured into NH$_4$Cl 10%, then extracted with CH$_2$Cl$_2$. The organic layer was dried over MgSO$_4$, filtered and the solvent was evaporated. The crude product was purified by chromatography over silica gel (eluent: CH$_2$Cl$_2$/methanol/NH$_4$OH: from 99:1:0.1 to 95:5:0.5). The pure fractions were collected and the solvent was evaporated. Yield: 0.045 g (12%, 213° C.) of compound 37.

Method B

At −78° C., under a nitrogen atmosphere, n-butyllithium (1.14 ml, 3.5 eq) was added dropwise to a solution of thiazole (0.00159 mol, 3.5 eq) in 10 ml of tetrahydrofuran. This mixture was stirred one hour at −78° C. Next, a solution of intermediate L in 5 ml tetrahydrofuran was added dropwise and the mixture was stirred for two hours at −78° C. and then at room temperature overnight. The reaction mixture was poured into NH$_4$Cl 10% and extracted with a mixture of CH$_2$Cl$_2$/tetrahydrofuran/methanol. The organic layer was dried over MgSO$_4$, filtered and the solvent evaporated. The crude product was purified by chromatography over silica gel (eluent: CH$_2$Cl$_2$/methanol/NH$_4$OH: from 98:2:0.2 to 92:8: 0.8). The pure fractions were collected and the solvent was evaporated. Yield: 0.073 g (30%, 134° C.) of compound 38.

TABLE 5

| Compound N° | R$^{5d}$ | Method | Phys. data, stereochemistry and yield |
|---|---|---|---|
| 36 | —CH=CH$_2$ (isopropenyl) | A | (E/Z: 85/15); 13% |
| 37 | —CH$_3$ | A | (E); 12%; 213° C. |
| 38 | thiazol-2-yl | B | (E/Z: 83/17); 30%. 134° C. |

EXAMPLE 4

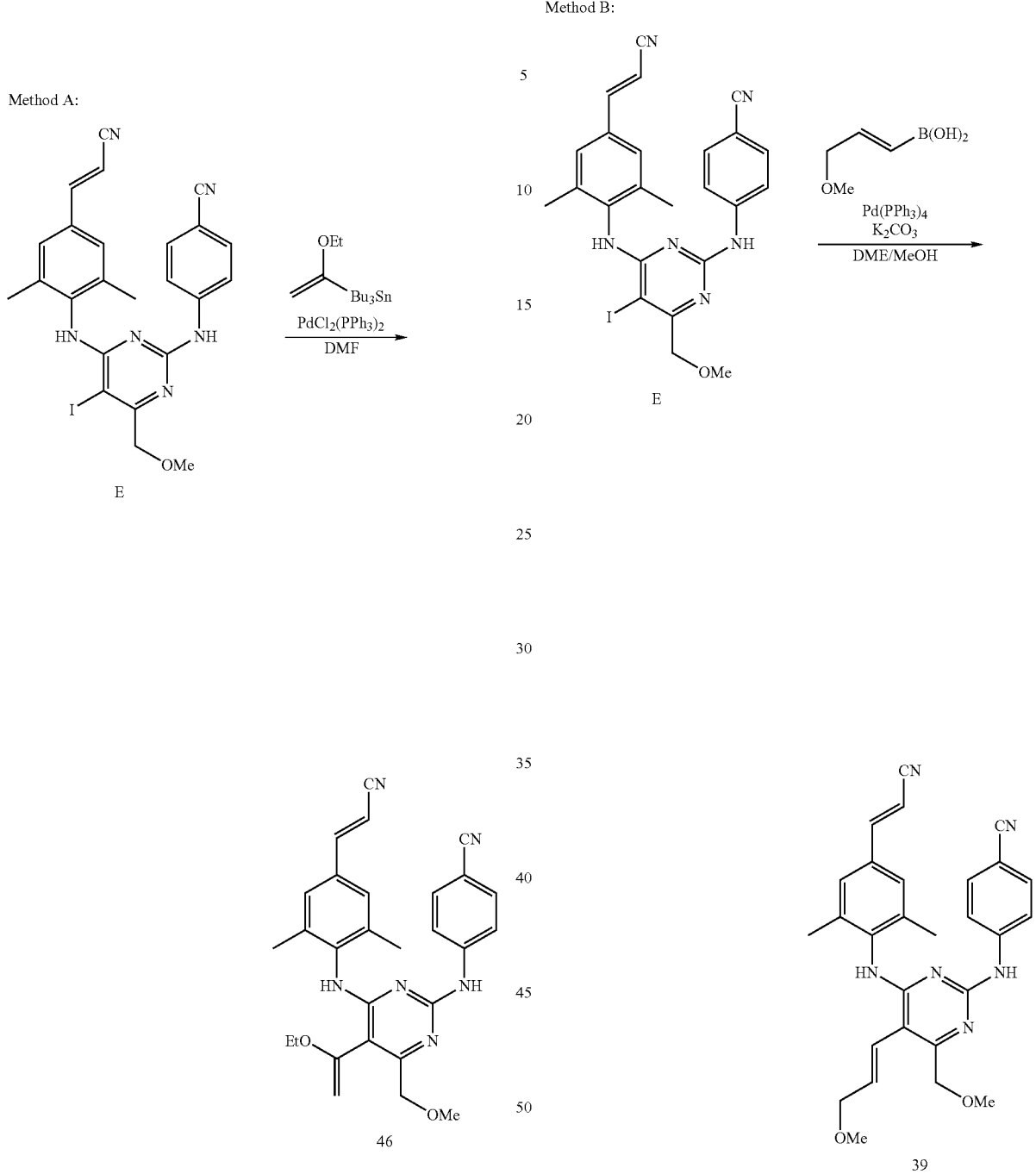

Method A:

To a solution of E (0.5 g, 0.93 mmol) in dimethyl formamide (6 ml), prepared as described in example 1, was added successively tributyl-(1-ethoxyvinyl)-stannane (1.86 mmol, 2 eq) and $PdCl_2(PPh_3)_2$ (0.19 mmol, 0.2 eq). The resulting mixture was stirred at 110° C. overnight. An aqueous solution of KF was added and the mixture was stirred 15 min then filtered over a celite pad and washed with $CH_2Cl_2$. The residue was extracted with $CH_2Cl_2$. The combined organic layers were washed with water, and then dried over $MgSO_4$ and filtered. The solvent was evaporated and the resulting mixture was purified by column chromatography (Kromasil 5 μm 250×30 μm, eluent: $CH_2Cl_2$/methanol 98:2) to give 0.089 g of pure product 46 (20% yield, melting point: 102° C.).

Method B:

To a solution of E (0.27 g, 0.52 mmol) in a 5:1 mixture of dimethyl ether/methanol (19 ml), was added successively the (E)-3-methoxypropene boronic acid (1.5 mmol, 3 eq), $Pd(PPh_3)_4$ (0.11 mmol, 0.2 eq) and a 2 N $K_2CO_3$ (2.5 mmol, 5 eq). The resulting mixture was stirred at reflux overnight. 10% $K_2CO_3$ solution was added and the mixture was filtered over a celite pad and washed with $CH_2Cl_2$. The residue was extracted with $CH_2Cl_2$/tetrahydrofuran. The combined organic layers were dried over $MgSO_4$ and filtered. The solvent was evaporated and the resulting mixture was purified by column chromatography (10 μm, eluent: $CH_2Cl_2$/methanol 99:1) to give 0.079 g of pure product 39 (33% yield).

Method C:

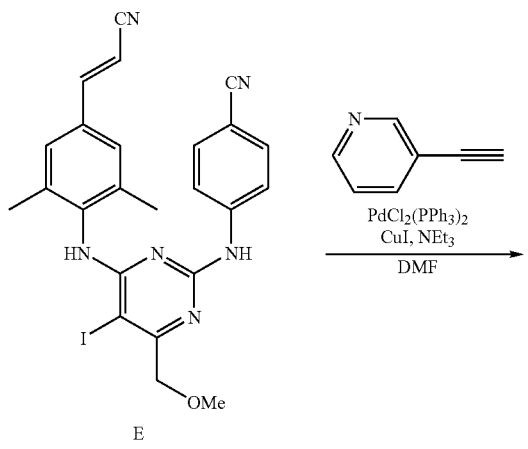

Method D:

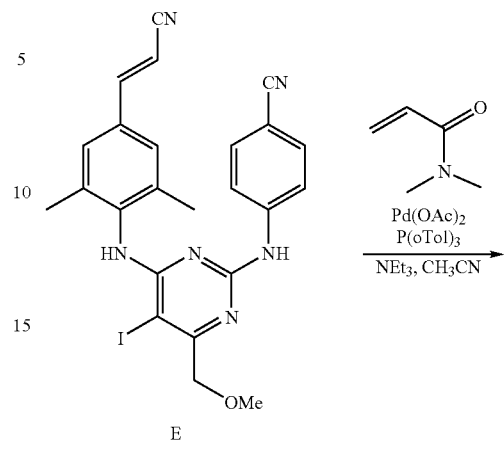

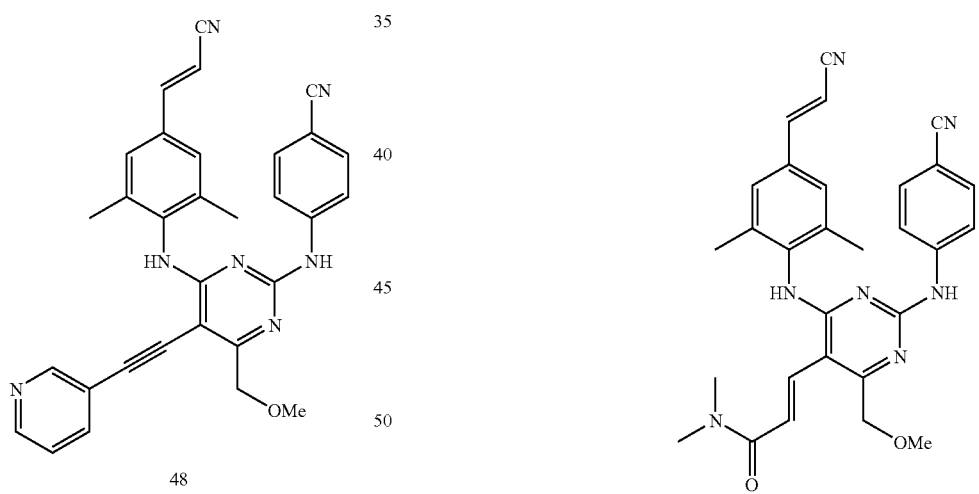

To a solution of E (1 g, 1.9 mmol) in dimethyl formamide (30 ml), was added successively 3-ethynylpyridine (5.7 mmol, 3 eq.), PdCl$_2$(PPh$_3$)$_2$ (0.19 mmol, 0.1 eq.), CuI (3.8 mmol, 2 eq.) and triethylamine (5.7 mmol, 3 eq.). The resulting mixture was stirred at reflux overnight. 10% K$_2$CO$_3$ solution was added and the mixture was filtered over a celite pad and washed with CH$_2$Cl$_2$. The residue was extracted with CH$_2$Cl$_2$/tetrahydrofuran. The combined organic layers were dried over MgSO$_4$ and filtered. The solvent was evaporated and the resulting mixture was purified by column chromatography (10 µm, eluent: CH$_2$Cl$_2$/methanol/NH$_4$OH 98:2:0.2) to give 0.29 g of pure product 48 (30% yield, melting point: 210° C.).

To a solution of E (0.25 g, 0.47 mmol) in acetonitrile (5 ml), was added successively N,N-dimethylacrylamide (4.7 mmol, 10 eq.), Pd(OAc)$_2$ (0.05 mmol, 0.1 eq.), tris(4-methylphenyl) phosphine (P(oTol)$_3$) (0.24 mmol, 0.5 eq.) and triethylamine (2.8 mmol, 6 eq.). The resulting mixture was stirred at 115° C. overnight and was then filtered over a celite pad, rinsed with water. The residue was extracted with CH$_2$Cl$_2$. The combined organic layers were dried over MgSO$_4$ and filtered. The solvent was evaporated and the resulting mixture was purified by column chromatography (3.5 µm, eluent: CH$_2$Cl$_2$/methanol/NH$_4$OH 99:1:0.1 to 93:7:0.7) to give 0.098 g of pure product 40 (41% yield).

Method E:

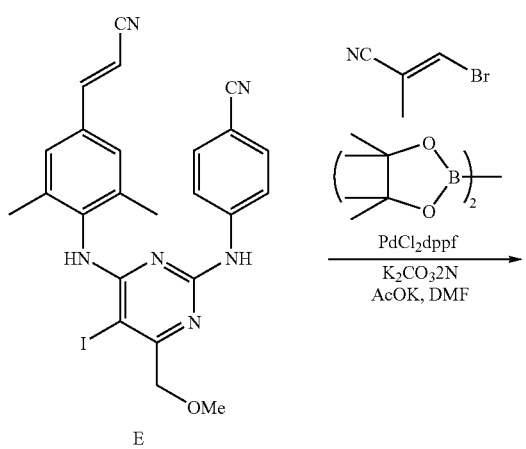

To a solution of E (0.8 g, 1.5 mmol) in dimethyl formamide (5 ml), was added successively bis(pinacolato)diboron (1.8 mmol, 1.2 eq.), PdCl$_2$dppf (PdCl$_2$ 1,1'-bis(diphenylphosphino)ferrocene) (0.075 mmol, 0.05 eq.) and potassium acetate (4.5 mmol, 3 eq.). The resulting mixture was stirred at 85° C. overnight. A solution of 3-bromo-2-methylacrylonitrile (3.0 mmol, 2 eq.), PdCl$_2$dppf (0.075 mmol, 0.05 eq.), and K$_2$CO$_3$ (7.5 mmol, 3 eq.) in dimethyl formamide (5 ml) was then added and the whole mixture was stirred at 115° C. for 24 hours. After cooling down, the resulting mixture was filtered over a celite pad, rinsed with water. The residue was extracted with CH$_2$Cl$_2$. The combined organic layers were dried over MgSO$_4$ and filtered. The solvent was evaporated and the resulting mixture was purified by column chromatography (3.5 μm, eluent: CH$_2$Cl$_2$/methanol 100:0 to 98:2; then 5 μm, eluent: CH$_2$Cl$_2$/methanol/NH$_4$OH 99:1:0.1 to 95:5:0.5) to give 0.028 g of pure product 42 (4% yield).

TABLE 6

| Compound N° | R$^5$ | Method | Phys. data, stereochemistry and yield |
|---|---|---|---|
| 39 | ![CH=CH-CH2-OMe] | B | E/Z 75/25 33% yield mp: — |
| 40 | ![CH=CH-C(O)NMe2] | D | 41% yield mp: — |
| 41 | ![CH=CH-C(O)NH2] | D | 10% yield mp: — |
| 42 | ![CH=C(CH3)-CN] | E | 4% yield mp: — |
| 43 | ![CH=CH-C6H4-CF3] | B | E/Z 86/14 41% yield mp: — |
| 44 | ![CH=CH-C6H4-CH3] | B | E 49% yield mp: 139° C. |

TABLE 6-continued

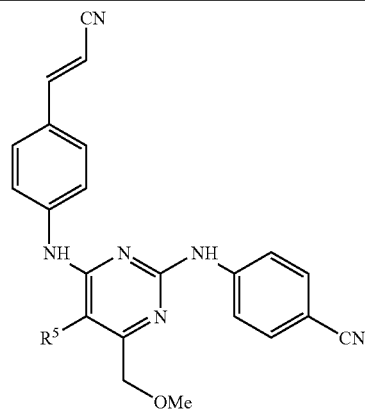

| Compound N° | R⁵ | Method | Phys. data, stereochemistry and yield |
|---|---|---|---|
| 45 | (4-MeO-phenyl)-CH=CH-CH(CH₃)- | B | E, 33% yield, mp: 207° C. |
| 46 | (EtO)(CH₃)C=CH- | A | E, 20% yield, mp: 102° C. |
| 47 | EtO-CH(OEt)-C≡C-C(CH₃)₂- | C | E/Z 83/17, 13% yield, mp: — |
| 48 | (pyridin-3-yl)-C≡C-C(CH₃)₂- | C | E/Z 98/2, 30% yield, mp: 210° C. |

Antiviral Spectrum:

Compounds of the invention were tested for their potency against wild type virus and clinically isolated HIV strains harboring one or more mutations associated with resistance to reverse transcriptase inhibitors. Antiviral activity was evaluated using a cellular assay performed according to the following procedure.

The human T-cell line MT4 was engineered with Green Fluorescent Protein (GFP) and a HIV-specific promoter, HIV-1 long terminal repeat (LTR). This cell line, designated MT4 LTR-EGFP, can be used for the in vitro evaluation of anti-HIV activity of investigational compounds. In HIV-1 infected cells, the Tat protein is produced, which upregulates the LTR promotor and eventually leads to stimulation of the GFP reporter production, allowing to measure ongoing HIV-infection fluorometrically.

Analogously, MT4 cells were engineered with GFP and the constitutional cytomegalovirus (CMV) promotor. This cell line was designated MT4 CMV-EGFP, and can be used for the in vitro evaluation of cytotoxicity of investigational compounds. In this cell line, GFP levels are comparably to those of infected MT4 LTR-EGFP cells. Cytotoxic investigational compounds reduce GFP levels of mock-infected MT4 CMV-EGFP cells.

Effective concentration values such as 50% effective concentration (EC50) can be determined and are usually expressed in μM. An EC50 value is defined as the concentration of test compound that reduces the fluorescence of HIV-infected cells by 50%. The 50% cytotoxic concentration (CC50 in μM) is defined as the concentration of test compound that reduces fluorescence of the mock-infected cells by 50%. The ratio of CC50 to EC50 is defined as the selectivity index (SI) and is an indication of the selectivity of the anti-HIV activity of the inhibitor. The ultimate monitoring of HIV-1 infection and cytotoxicity was done using a scanning microscope. Image analysis allowed very sensitive detection of viral infection. Measurements were done before cell necrosis, which usually takes place about five days after infection, in particular measurements were performed three days after infection.

The columns IIIB, L100I, etc. in the table list the $pEC_{50}$ (−log EC50) values against various strains IIIB, L100I, etc.; pSI lists the −log SI values.

Strain IIIB is wild type HIV strain.

"MDR" refers to a strain that contains mutations L100I, K103N, Y181C, E138G, V179I, L2214F, V278V/I and A327A/V in HIV reverse transcriptase.

| Compound N° | IIIB | pSI (IIIB) | MDR | L100I + K103N | K103N + Y181C | K103N + Y181C |
|---|---|---|---|---|---|---|
| 1 | 7.89 | >3.28 | 5.62 | 7.20 | 7.03 | 7.08 |
| 2 | 8.52 | 3.65 | 6.62 | 8.38 | 7.67 | 7.80 |
| 3 | 8.48 | >3.88 | 6.45 | 8.03 | 7.53 | 7.65 |
| 4 | 8.34 | 3.73 | 6.86 | 8.42 | 7.81 | 7.73 |
| 5 | 8.36 | >3.76 | 6.49 | 8.30 | 7.67 | 7.60 |
| 6 | 8.44 | 3.61 | 7.05 | 8.44 | 7.78 | 7.76 |
| 7 | 8.43 | 3.75 | 7.04 | 8.62 | 7.91 | 7.90 |
| 8 | 8.54 | 3.13 | 7.07 | 7.57 | 7.83 | 7.88 |
| 9 | 8.28 | 3.55 | 6.45 | 7.26 | 7.43 | 7.53 |
| 10 | 8.46 | 3.44 | 7.30 | 8.10 | 7.78 | 7.84 |
| 11 | 8.47 | 3.59 | 7.24 | 7.43 | 7.68 | 7.83 |
| 12 | 8.25 | 3.59 | 6.68 | 7.42 | 7.68 | 7.58 |
| 13 | 8.41 | 3.32 | 5.69 | 6.81 | 7.07 | 7.20 |
| 14 | 8.41 | 3.70 | 6.42 | 6.67 | 7.10 | 7.21 |
| 15 | 8.55 | 3.52 | 6.43 | 7.24 | 7.67 | 7.82 |
| 16 | 8.90 | 4.22 | 7.03 | 7.55 | 7.84 | 7.84 |
| 17 | 7.43 | >2.83 | 5.19 | 6.59 | 6.31 | 6.43 |
| 18 | 8.23 | >3.63 | 6.42 | 6.97 | 7.04 | 7.13 |
| 19 | 8.59 | 3.83 | 6.97 | 7.38 | 7.85 | 7.78 |
| 20 | 8.83 | 3.81 | 7.03 | 7.28 | 7.67 | 7.77 |
| 21 | 7.49 | 2.53 | 5.44 | 6.31 | 6.28 | 6.48 |
| 22 | 7.27 | >2.66 | 5.64 | 6.22 | 6.18 | 6.30 |
| 23 | 8.62 | 3.87 | 6.85 | 7.81 | 7.65 | 7.66 |
| 24 | 8.66 | 3.96 | 6.72 | 7.99 | 7.65 | 7.71 |
| 25 | 8.72 | 4.02 | 6.27 | 7.19 | 7.12 | 7.14 |
| 26 | 7.62 | >3.02 | 5.02 | 5.61 | 5.55 | 5.74 |
| 27 | 8.21 | >3.61 | 5.21 | 5.79 | 5.77 | 5.88 |
| 29 | 7.83 | >3.23 | 6.72 | 7.01 | 7.14 | 7.35 |
| 30 | 7.84 | >3.24 | 5.79 | 6.67 | 6.71 | 7.04 |
| 31 | 8.41 | 3.39 | 6.81 | 6.64 | 7.07 | 7.70 |
| 32 | 8.48 | 3.43 | 7.05 | 7.80 | 7.71 | 7.71 |
| 33 | 8.40 | 3.54 | 5.91 | 7.03 | 7.21 | 7.20 |
| 34 | 8.38 | 3.22 | 5.81 | 6.49 | 6.98 | 7.12 |
| 35 | 8.54 | 3.76 | 6.18 | 7.09 | 7.43 | 7.16 |
| 36 | 8.58 | 3.85 | 7.18 | 8.46 | 8.06 | 7.90 |
| 37 | 8.84 | 3.95 | 6.98 | 8.61 | 8.22 | 7.94 |
| 38 | 8.57 | 3.81 | 6.76 | 8.43 | 7.91 | 7.92 |

The invention claimed is:
1. A compound of formula

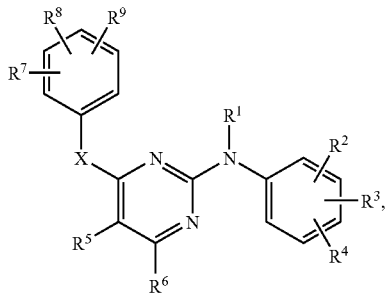

a pharmaceutically acceptable addition salt or a stereochemically isomeric form thereof, wherein:

each $R^1$ independently is hydrogen; aryl; formyl; $C_{1-6}$alkylcarbonyl; $C_{1-6}$alkyl; $C_{1-6}$alkyloxycarbonyl;

$R^2$, $R^3$, $R^7$ and $R^8$ independently are hydrogen; hydroxy; halo; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^{10}$; $C_{1-6}$alkyl optionally substituted with halo, cyano or —C(=O)$R^{10}$; $C_{2-6}$alkenyl optionally substituted with halo, cyano or —C(=O)$R^{10}$; $C_{2-6}$alkynyl optionally substituted with halo, cyano or —C(=O)$R^{10}$;

$R^4$ and $R^9$ independently are hydroxy; halo; $C_{3-7}$cycloalkyl; $C_{1-6}$alkyloxy; carboxyl; $C_{1-6}$alkyloxycarbonyl; formyl; cyano; nitro; amino; mono- or di($C_{1-6}$alkyl)amino; polyhalo$C_{1-6}$alkyl; polyhalo$C_{1-6}$alkyloxy; —C(=O)$R^{10}$; cyano; —S(=O)$_r R^{10}$; —NH—S(=O)$_2 R^{10}$; —NHC(=O)H; —C(=O)NHNH$_2$; —NHC(=O)$R^{10}$; Het; $C_{1-6}$alkyl optionally substituted with halo, cyano, amino, mono- or di($C_{1-6}$alkyl)amino, —C(=O)—$R^{10}$, Het or with $C_{1-6}$alkyloxy; $C_{2-6}$alkenyl optionally substituted with halo, cyano, amino, mono- or di($C_{1-6}$alkyl)amino, —C(=O)—$R^{10}$, Het or with $C_{1-6}$alkyloxy; $C_{2-6}$alkynyl optionally substituted with halo, cyano, amino, mono- or di($C_{1-6}$alkyl)amino, —C(=O)—$R^{10}$, Het or with $C_{1-6}$alkyloxy;

$R^5$ is $C_{2-6}$alkenyl or $C_{2-6}$alkynyl both substituted with cyano, aminocarbonyl, mono- or di($C_{1-6}$alkyl)aminocarbonyl, aryl, pyridyl, thienyl, furanyl, or with one or two $C_{1-6}$alkyloxy groups; or $R^5$ is Het; —C(=O)NR$^{5a}$R$^{5b}$; or —CH(OR$^{5c}$)R$^{5d}$; wherein $R^{5a}$ is $C_{1-6}$alkyloxy; $C_{2-6}$alkenyl; $C_{3-7}$cycloalkyl; or $C_{1-6}$alkyl substituted with hydroxy, amino, mono- or di($C_{1-6}$alkyl)amino, $C_{1-6}$alkylcarbonylamino, halo, cyano, aryl, pyridyl, thienyl, furanyl, tetrahydrofuranyl, pyrrolidinyl, piperidinyl, morpholinyl, piperazinyl, piperazinyl optionally substituted with $C_{1-6}$alkyl, $C_{1-6}$alkylcarbonyl, or with hydroxy$C_{1-6}$alkyl; or $R^{5a}$ is $C_{1-6}$alkyl substituted with one or two $C_{1-6}$alkyloxy;

$R^{5b}$ is hydrogen or $C_{1-6}$alkyl; or $R^{5a}$ and $R^{5b}$ taken together with the nitrogen atom to which they are substituted form pyrrolidinyl; piperidinyl optionally substituted with aminocarbonyl, hydroxy, or with $C_{1-6}$alkyloxy; morpholinyl; piperazinyl; piperazinyl optionally substituted with $C_{1-6}$alkyl, $C_{1-6}$alkylcarbonyl, or with hydroxy$C_{1-6}$alkyl;

$R^{5c}$ is hydrogen, $C_{1-6}$alkyl, Het;

$R^{5d}$ is $C_{1-6}$alkyl, $C_{2-6}$alkenyl, $C_{2-6}$alkynyl, aryl, or Het;

$R^6$ is $C_{1-6}$alkoxyC$_{1-6}$alkyl;

each $R^{10}$ independently is $C_{1-6}$alkyl, amino, mono- or di($C_{1-6}$alkyl)amino or polyhalo$C_{1-6}$alkyl;

X is —NR$^1$—, —O—, —CH$_2$—, or —S—;

each r independently is 1 or 2;

each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from $C_{1-6}$alkyl, halo, hydroxy, cyano, $C_{1-6}$alkyloxy, and $C_{2-6}$alkenyl substituted with halo, hydroxy or with cyano;

each aryl independently is phenyl or phenyl substituted with one, two, three, four or five substituents each independently selected from halo, hydroxy, mercapto, $C_{2-6}$alkenyl, $C_{2-6}$alkynyl, hydroxy$C_{1-6}$alkyl, amino$C_{1-6}$alkyl, mono or di($C_{1-6}$alkyl)amino-$C_{1-6}$alkyl, $C_{1-6}$alkylcarbonyl, $C_{3-7}$cycloalkyl, $C_{1-6}$alkyloxy, phenyl$C_{1-6}$alkyloxy, $C_{1-6}$alkyloxycarbonyl, aminosulfonyl, $C_{1-6}$alkylsulfonyl, cyano, nitro, polyhalo$C_{1-6}$alkyl, polyhalo$C_{1-6}$alkyloxy, aminocarbonyl, phenyl or Het.

2. The compound of claim 1 wherein the compound of formula (I) has the following structure:

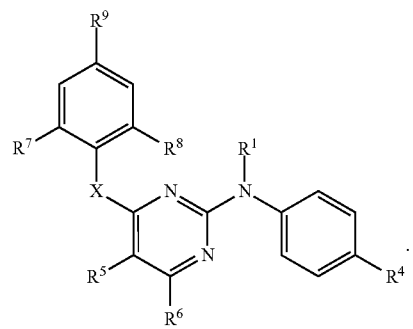

3. The compound of claim 1, wherein $R^4$ and $R^9$ independently are cyano; $C_{1-6}$alkyl substituted with cyano; $C_{2-6}$alkenyl substituted with cyano.

4. The compound of claim 1, wherein $R^2$, $R^3$, $R^7$ and $R^8$ independently are hydrogen; halo; $C_{1-6}$alkyl; cyano.

5. The compound of claim 1, wherein $R^9$ is a radical —CH$_2$—CH$_2$—CN, —CH=CH—CN, or —C≡C—CN.

6. The compound of claim 5, wherein $R^9$ is a radical (E)-CH=CH—CN.

7. The compound of claim 1, wherein $R^4$ is cyano.

8. The compound of claim 1, wherein $R^1$ is hydrogen.

9. The compound of claim 1, wherein (a) $R^5$ is $C_{2-6}$alkenyl or $C_{2-6}$alkynyl both substituted with cyano, aminocarbonyl, mono- and di($C_{1-6}$alkyl)aminocarbonyl, aryl, pyridyl, or with one or two $C_{1-6}$alkyloxy groups; Het; —C(=O)NR$^{5a}$R$^{5b}$; —CH(OR$^{5c}$)R$^{5d}$;

wherein $R^{5a}$ is $C_{1-6}$alkyloxy; $C_{2-6}$alkenyl; $C_{3-7}$cycloalkyl; or $C_{1-6}$alkyl substituted with mono- and di($C_{1-6}$alkyl) amino, $C_{1-6}$alkylcarbonylamino, cyano, aryl, pyridyl, thienyl, tetrahydrofuranyl, morpholinyl, piperazinyl, piperazinyl optionally substituted with $C_{1-6}$alkyl or with hydroxyC$_{1-6}$alkyl; or R$^{5a}$ is C$_{1-6}$alkyl substituted with one or two C$_{1-6}$alkyloxy;

R$^{5b}$ is hydrogen or C$_{1-6}$alkyl; or

R$^{5a}$ and R$^{5b}$ taken together with the nitrogen atom to which they are substituted form piperidinyl optionally substituted with aminocarbonyl or hydroxy; piperazinyl optionally substituted with C$_{1-6}$alkyl or hydroxyC$_{1-6}$alkyl;

R$^{5c}$ is hydrogen;

R$^{5d}$ is C$_{1-6}$alkyl, C$_{2-6}$alkenyl, aryl, pyridyl, or thiazolyl.

10. The compound of claim 1, wherein X is —NH—.

11. The compound of claim 1, wherein each Het independently is pyridyl, thienyl, furanyl, oxazolyl, thiazolyl.

12. A pharmaceutical composition comprising an effective amount of a compound of formula (I) as defined in claim 1 and a carrier.

* * * * *